(12) United States Patent
Mondoulet et al.

(10) Patent No.: US 8,202,533 B2
(45) Date of Patent: Jun. 19, 2012

(54) IMMUNOTHERAPEUTIC METHOD FOR INCREASING GROUNDNUT TOLERANCE IN A SUBJECT

(75) Inventors: Lucie Mondoulet, Chatillon (FR);
Christophe Dupont, Clamart (FR);
Pierre-Henri Benhamou, Paris (FR);
Bertrand Dupont, Aix En Provence (FR)

(73) Assignee: DBV Technologies, Bagneux (FR)

( * ) Notice: Subject to any disclaimer, the term of this patent is extended or adjusted under 35 U.S.C. 154(b) by 374 days.

(21) Appl. No.: 12/628,077

(22) Filed: Nov. 30, 2009

(65) Prior Publication Data

US 2010/0136093 A1 Jun. 3, 2010

Related U.S. Application Data

(63) Continuation-in-part of application No. PCT/EP2008/066737, filed on Dec. 3, 2008.

(60) Provisional application No. 61/084,305, filed on Jul. 29, 2008.

(30) Foreign Application Priority Data

Dec. 3, 2007 (FR) ...................................... 07 59503

(51) Int. Cl.
*A61F 13/02* (2006.01)
*A61K 9/70* (2006.01)
(52) U.S. Cl. ....................................................... 424/449
(58) Field of Classification Search ........................ None
See application file for complete search history.

(56) References Cited

U.S. PATENT DOCUMENTS 7,722,897 B2 * 5/2010 Dupont et al. ................ 424/448

FOREIGN PATENT DOCUMENTS

| EP | 1 031 346 A1 | 8/2000 |
| WO | WO 02/071950 A1 | 9/2002 |
| WO | WO 02/093998 A2 | 11/2002 |
| WO | WO 2007/122226 A2 | 11/2007 |

OTHER PUBLICATIONS

Mondoulet e al, Viaskin®:Epicutaneous Immunotherapy fpr Treating Food Allergies, Drug Development & Delivery, Jun. 2011, vol. 11, No. 5.*
Adel-Patient et al., *Peanut- and cow's milk-specific IgE. Th2 cells and local anaphylactic reaction are induced in Balb/c mice orally sensitized with cholera toxin*, 60(5) Allergy 658, 658-64 (2005).
Becker et al., *Four novel recombinant peanut allergens: more information, more problems*, 124 Int. Arch. Allergy Immunol. 100, 100-02 (2001).
Burks et al., *Identification of a major peanut allergen, Ara h I, in patients with atopic dermatitis and positive peanut challenges*, 88 J. Allergy Clin. Immunol. 172, 172-79 (1991).

(Continued)

*Primary Examiner* — Carlos Azpuru
(74) *Attorney, Agent, or Firm* — Jones Day; Nicola A. Pisano; Jaime D. Choi

(57) ABSTRACT

The present invention describes a new method for progressive desensitization of a subject to groundnut. More specifically, the invention relates to the immunotherapeutic method for increasing groundnut tolerance in an allergic subject using epicutaneous administration. The present invention is also relative to the use of a skin patch device for progressive desensitization of a subject to groundnut.

21 Claims, 14 Drawing Sheets

OTHER PUBLICATIONS

Burks et al., *Identification and characterization of a second major peanut allergen, Ara h II, with use of the sera of patients with atopic dermatitis and positive peanut challenge*, 90 J. Allergy Clin. Immunol. 962, 962-69 (1992).

Burks et al., *Recombinant Peanut Allergen Ara h I Expression and IgE Binding in Patients with Peanut Hypersensitivity*, 96 J. Clin. Invest. 1715, 1715-21 (1995).

Anonymous, *DBV Company Profile*, Internet Article, Jan. 3, 2008, 2 pages, XP002521667.

Francis et al., Grass pollen immunotherapy: *IL-10 induction and suppression of late responses precedes IgG4 inhibitory antibody activity*, 121(5) J. Allergy Clin. Immunol. 1120, 1 120-1 125 (2008).

Hoymann Hg., *New developments in lung function measurements in rodents*, 2 Exp. Toxicol. Pathol. 5. 5-11 (2006).

Hufnagl et al., *Airway inflammation induced after allergic poly-sensitization can be prevented by mucosal but not by systemic administration of poly-peptides*, 38 Clin. Exp. Allergy 1192, 1192-1202 (2008).

International Search Report for PCT/EP2008/066737, 3 pages, mailed Apr. 15, 2009.

Koppelman et al., *Purification and immunoglobulin E-binding properties of peanut allergen Ara h 6: evidence for cross-reactivity with Ara h 2*, 35(4) Clin. Exp. Allergy 490, 490-97 (2005).

Langranderie et al., *Mycobacterium bovis BCG killed by extended freeze-drying reduces airway hyperresponsiveness in 2 animal models*, 121(2) J. Allergy Clin. Immunol. 471, 471-78 (2008).

Mittag et al., *Ara h 8. a Bet v 1-homologous allergen from peanut, is a major allergen in patients with combined birch pollen and peanut allergy*, 114 J. Allergy Clin. Immunol. 1410, 1410-17 (2004).

Mondoulet et al., *Epicutaneous immunotherapy for peanut allergy: a preclinical study*, 63(88) Allergy 10, 10-11 (2008).

Pajno et al., *Children's compliance with allergen immunotherapy according to administration routes*, 116(6) J. Allergy Clin. Immunol. 1380, 1380-81 (2005).

Poulsen et al., *Comparison of intestinal anaphylactic reactions in sensitized mice challenged with untreated bovine milk and homogenized bovine milk*, 45(5) Allergy 321, 321-26 (1990).

\* cited by examiner

IMMUNOTHERAPEUTIC METHOD FOR INCREASING GROUNDNUT TOLERANCE IN A SUBJECT

CROSS-REFERENCE TO RELATED APPLICATIONS

This application is a continuation-in-part of International Patent Application No. PCT/EP2008/066737, filed on Dec. 3, 2008, the entire contents of which are incorporated by reference herein, which claims the benefit of French Patent Application No. 0759503, filed on Dec. 3, 2007, the entire contents of which are incorporated by reference herein and U.S. Provisional Patent Application No. 61/084,305, filed on Jul. 29, 2008, the entire contents of which are incorporated by reference herein.

FIELD OF THE INVENTION

The present invention relates to new immunotherapeutic methods for increasing tolerance to groundnut in a subject. Particularly, the present invention discloses the use of a skin patch device for progressive desensitization of a subject to groundnut.

BACKGROUND OF THE INVENTION

Peanut allergy is one of the most common and serious of the immediate hypersensitivity reactions to foods in terms of persistence and severity of reaction. In fact, this allergy is estimated to be involved in the majority of fatal and near-fatal food-related anaphylaxis in all age groups. The prevalence of this allergy has doubled in the last decade and it now affects between 0.6% and 1.2% of the general population. Sicherer et al., *Prevalence of the peanut and tree nut allergy in the United States determined by means of random digit dial telephone survey: a 5-year follow-up study*, 112(6) J. ALLERGY CLIN. IMMUNOL. 1203, 1203-07 (2003).

This allergy tends to present early in life and only 20% of allergic children become tolerant to peanut. Skolnick et al., *The natural history of peanut allergy*, 107(2) J. ALLERGY CLIN. IMMUNOL. 367, 367-74 (2001). Sensitization generally occurs in the gastrointestinal tract but can also occur as a consequence of direct or cross-sensitization by inhalation exposure to peanut or cross-reactive environmental antigens such as pollen.

The allergic reaction provoked by peanuts is strictly an IgE mediated type I hypersensitivity reaction. The IgE-allergen complex causes mast cell receptors to cross-link inducing a signal transduction cascade that ends in degranulation and release of a variety of mediators that give rise to the clinical symptoms of peanut hypersensitivity.

The major peanut allergens are seed storage proteins. Although 9 peanut allergens, namely Ara h 1 to Ara h 9, have been reported, Ara h 1, Ara h 2, and Ara h 3 are classified as the major peanut allergens because they are generally recognized by more than 50% of peanut-allergic patients. Burks et al., *Identification and characterization of a second major peanut allergen, Ara h II, with use of the sera of patients with atopic dermatitis and positive peanut challenge*, 90 J. ALLERGY CLIN. IMMUNOL. 962, 962-69 (1992); Burks et al., *Identification of a major peanut allergen, Ara h I, in patients with atopic dermatitis and positive peanut challenges*, 88 J. ALLERGY CLIN. IMMUNOL. 172, 172-79 (1991); Rabjohn et al., *Molecular cloning and epitope analysis of the peanut allergen Ara h 3*, 103 J. CLIN. INVEST. 535, 535-42 (1999); Koppelman et al., *Purification and immunoglobulin E-binding properties of peanut allergen Ara h 6: evidence for cross-reactivity with Ara h 2*, 35(4) CLIN. EXP. ALLERGY 490, 490-97 (2005); Koppelman et al., *Quantification of major peanut allergens Ara h 1 and Ara h 2 in the peanut varieties Runner, Spanish, Virginia, and Valencia, bred in different parts of the world*, 56(2) ALLERGY 132, 132-37 (2001); Mittag et al., *Ara h 8, a Bet v 1-homologous allergen from peanut, is a major allergen in patients with combined birch pollen and peanut allergy*, 114 J. ALLERGY CLIN. IMMUNOL. 1410, 1410-17 (2004); Becker et al., *Four novel recombinant peanut allergens: more information, more problems*, 124 INT. ARCH. ALLERGY IMMUNOL. 100, 100-02 (2001); Lauer et al., *Abstracts of the XXVII EAACI Congress of the European Academy of Allergology and Clinical Immunology*, 63(88) ALLERGY 158, 158-611 (2008).

Preventive treatment of this allergy consists of avoidance, which is very difficult because of the widespread and often disguised use of peanuts in the food industry. Current pharmacotherapies (antihistamines and corticosteroids) can be used to reduce the symptoms of allergic disease but do not prevent allergic reaction.

Immunotherapy is the only available treatment that can modify the natural course of the allergic disease, by reducing sensitivity to allergens. For immunotherapy, a dose of an allergen is given in order to progressively induce an immune response characterized by tolerance to the antigen/allergen, also known as desensitization. This method is particularly indicated for patients with severe allergic IgE-dependent reactions.

Even though immunotherapy has been in practice for more than 90 years, the exact mechanism of its action is still not clear. In humans, it involves (i) an increase of IgG, in particular IgG4 which is a blocking antibody that may block IgE mediated mechanisms by inhibiting the release of inflammatory mediators from mast cells and basophils, (ii) an increase of regulatory T cells (Treg) leading to a better balance of the Th2/Th1 profile, and (iii) the production of T cells producing IL-10, also known as human cytokine synthesis inhibitory factor (CSIF), which counteracts the inflammatory effect of mast cells and promotes the production of IgG4.

Until now, the immunotherapy could be administered by subcutaneous, sublingual or intra-nasal routes.

Subcutaneous immunotherapy is the most common treatment used by allergists. Nevertheless, this method is quite expensive and requires a specialized practitioner for each injection. A major drawback of subcutaneous immunotherapy is its allergic side effects. These side effects can be either local or systemic. Groundnut allergy immunotherapies using subcutaneous route have been demonstrated to induce a high rate of adverse systemic reaction (up to 50%). Nelson et al., *Treatment of anaphylactic sensitivity to peanuts by immunotherapy with injections of aqueous peanut extract*, 99 J. ALLERGY CLIN. IMMUNOL. 744, 744-51 (1997); Oppenheimer et al., *Treatment of peanut allergy with rush immunotherapy*, 90 J. ALLERGY CLIN. IMMUNOL. 256, 256-62 (1992). Systemic side effects are caused by allergen inadvertently being injected into small subcutaneous blood vessels, or allergens diffusing into the subcutaneous blood vessels. Allergens may be transported to other organs such as the lung or distant sites of the skin, where they can provoke asthma or hives. They also may cause anaphylaxis which can result in death. Consequently, allergies with high anaphylaxis risks, such as peanut allergy, cannot be treated by subcutaneous route.

Sublingual immunotherapy was accepted by WHO as a valid alternative to the subcutaneous route and should be used in all patients who require immunotherapy and do not accept the subcutaneous route of allergen administration. However, the dose of allergen required for sublingual immunotherapy is greater than subcutaneous immunotherapy and this method sometimes induces some local adverse effects such as oral pruritus, throat irritation, swelling of tongue or throat.

Intra-nasal immunotherapy is another alternative to the subcutaneous route which has been proven to be efficient for seasonal rhinitis and asthma treatment. Hufnagl et al., *Airway inflammation induced after allergic poly-sensitization can be prevented by mucosal but not by systemic administration of poly-peptides,* 38 Clin. Exp. Allergy 1192, 1192-1202 (2008). Nevertheless, this route is generally not well tolerated by patients and most of them prematurely interrupt their treatment. Pajno et al., *Children's compliance with allergen immunotherapy according to administration routes,* 116(6) J. ALLERGY CLIN. IMMUNOL. 1380, 1380-81 (2005).

Consequently, there is a need for an immunotherapy method for groundnut allergy treatment which is safe, efficient and well tolerated by patients.

SUMMARY OF THE INVENTION

The present invention provides a new method of immunotherapy to groundnut allergies. More specifically, the invention shows, for the first time, that efficient immunotherapy of groundnut allergies can be achieved through the epicutaneous route.

The present invention provides a new immunotherapeutic method for increasing tolerance in a subject to groundnut, which comprises repeatedly administering to said subject one or more proteins derived from groundnut via the epicutaneous route by means of a skin patch device comprising a backing, the periphery of said backing being adapted to create with the skin a hermetically closed chamber, wherein the backing bears on its skin facing side within the chamber said one or more proteins in a dose sufficient to induce an immune reaction in said subject following application of the patch device to the skin, said one or more proteins being removed from the backing following application of the patch device to the skin and thereafter delivered to the subject via the epicutaneous route, said administration leading, on repetition, to a progressive increase in tolerance in the subject to groundnut.

The invention also relates to a method for increasing tolerance to groundnut in a subject in need thereof, which method comprises the repeated epicutaneous administration, on intact skin of said subject, of an adjuvant-free groundnut allergen preparation, said administration allowing to increase tolerance to said allergen.

Preferably, administration is performed under conditions allowing prevention or reduction of mastocyte degranulation in said subject, or allowing a decrease in airway hyper-responsiveness of the subject.

The invention also relates to a method for preventing or reducing mastocyte degranulation in a subject allergic to an allergen, which method comprises the repeated epicutaneous administration, on intact skin of said subject, of an adjuvant-free preparation of said allergen, said administration allowing to prevent or reduce mastocyte degranulation in said subject.

The invention also relates to a method for preventing or reducing mastocyte degranulation in a subject allergic to groundnut, which method comprises the repeated epicutaneous administration, on intact skin of said subject, of an adjuvant-free groundnut allergen preparation, said administration allowing to prevent or reduce mastocyte degranulation in said subject.

The invention also relates to a method for reducing lung eosinophilia in a subject allergic to an allergen, which method comprises the repeated epicutaneous administration, on intact skin of said subject, of an adjuvant-free preparation of said allergen, said administration allowing to prevent or reduce lung eosinophilia in said subject.

The invention also relates to a method for reducing lung eosinophilia in a subject allergic to groundnut, which method comprises the repeated epicutaneous administration, on intact skin of said subject, of an adjuvant-free preparation of a groundnut allergen, said administration allowing to prevent or reduce lung eosinophilia in said subject.

The invention also relates to the use of an adjuvant-free preparation of an allergen for the manufacture of an adjuvant-free composition to prevent or reduce lung eosinophilia in a subject allergic to said allergen, by repeated application of said composition on intact skin of the subject.

The invention also relates to the use of an adjuvant-free preparation of an allergen for the manufacture of an adjuvant-free composition to prevent or reduce mastocyte degranulation in a subject allergic to said allergen, by repeated application of said composition on intact skin of the subject.

In a further aspect, the present invention concerns a skin patch device comprising a backing, the periphery of said backing being adapted to create with the skin a hermetically closed chamber, wherein the backing bears on its skin facing side within the chamber one or more proteins derived from groundnut in a dose sufficient to induce an immune reaction in a subject following application of the patch device to the skin, said one or more proteins derived from groundnut being removed from the backing following application of the patch device to the skin and thereafter delivered to the subject via the epicutaneous route.

In another aspect, the present invention also concerns a skin patch device comprising a backing, the periphery of said backing being adapted to create with the skin a hermetically closed chamber, wherein the backing bears on its skin facing side within the chamber one or more proteins derived from groundnut in a dose sufficient to induce an immune reaction in a subject following application of the patch device to the skin, said one or more proteins derived from groundnut being removed from the backing following application of the patch device to the skin and thereafter delivered to the subject via the epicutaneous route, for increasing tolerance in a subject to groundnut.

In another aspect, the present invention also concerns a patch kit comprising a plurality of skin patch devices, each of said devices comprising a backing, the periphery of said backing being adapted to create with the skin a hermetically closed chamber, wherein the backing bears on its skin facing side within the chamber one or more proteins derived from groundnut in a dose sufficient to induce an immune reaction in a subject following application of the patch device to the skin, said one or more proteins derived from groundnut being removed from the backing following application of the patch device to the skin and thereafter delivered to the subject via the epicutaneous route. The different patches of the kit may contain the same or a different amount of groundnut allergen thus making it possible to maintain or to increase/decrease the allergen doses over the course of the immunotherapeutic method of the invention.

The invention may be used in any subject, particularly any human subject, including children and adults. Preferably, the subject is allergic to groundnuts.

DETAILED DESCRIPTION OF THE INVENTION

Figure 1:
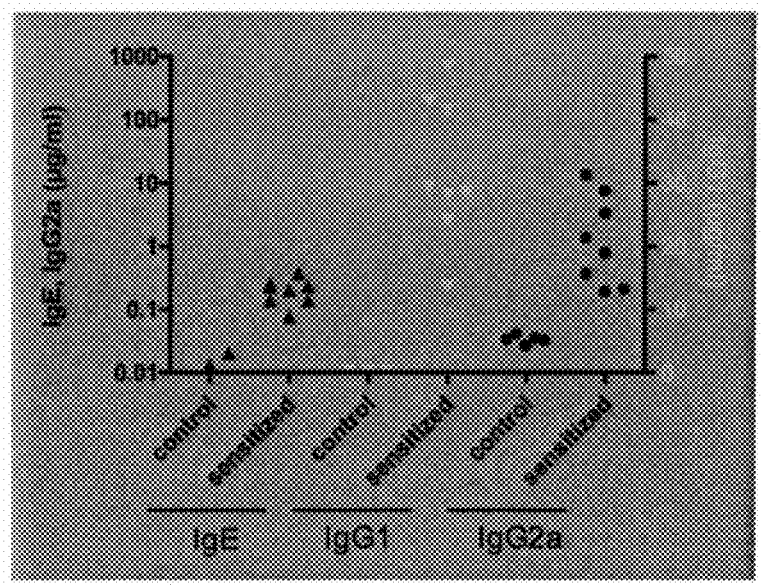
FIG. 1 is a graph that shows specific IgE, IgG1, IgG2a levels in mouse sera at the end of sensitization (day 43).

The present invention relates to an immunotherapeutic method for increasing groundnut tolerance in a subject using epicutaneous administration. This method is particularly safe for the patient considering that allergens have not been shown to cross the skin into the bloodstream. This approach could thus prevent severe allergic patients from the important risk of systemic or anaphylactic reactions during the immunotherapy protocol. Furthermore, the results obtained by the inventors show that desensitisation to groundnuts through the epicutaneous route according to this invention is at least as efficient as desensitisation using other routes of administration, in particular intradermal route.

In particular, the present invention shows that a specific immune reaction provoked by the skin application of groundnut allergens according to this invention induces a modification of the immune system of the subject and leads to a progressive increase in tolerance in the subject to groundnut.

The immunotherapeutic method of the invention involves the administration of a groundnut allergen composition to a subject via the epicutaneous route using particular patch devices, leading to tolerance.

As used in this specification, the term "epicutaneous route" means the administration of an allergen to a subject by application of this allergen on the skin. The epicutaneous route does not require the use of a needle, syringe or of any other means to perforate or to alter the integrity of the superficial layer of the epidermis. The allergen is maintained in contact with the skin for period of time and under conditions sufficient to allow the allergen to penetrate into the stratum corneum of the epidermis. This diffusion induces the migration and the activation of Langerhans cells thereby promoting an immune reaction.

The term "tolerance" is here defined as a reduction in immunological reactivity of a subject towards specific allergens.

As used in this specification, the term "groundnut" or "peanut" means a species in the legume family Fabaceae, for example Arachis. Peanuts are also known as earthnuts, goobers, goober peas, pindas, jack nuts, pinders, manila nuts and monkey nuts.

As used in the present specification, the term "groundnut allergen" refers to any protein or peptide derived from groundnut which is capable of evoking an allergic reaction. This allergen may be selected from natural or native allergens, modified natural allergens, synthetic allergens, recombinant allergens, allergoids, and mixtures or combinations thereof. Preferably, selected allergens are capable of causing an IgE-mediated immediate type hypersensitivity. The terms "polypeptide", "peptide" and "protein" are used interchangeably herein to refer to a polymer of amino acid residues. The terms apply to amino acid polymers in which one or more amino acid residue is a modified residue, or a non-naturally occurring residue, such as an artificial chemical mimetic of a corresponding naturally occurring amino acid, as well as to naturally occurring amino acid polymers.

In the present specification, the term "protein derived from groundnut" refers to any protein which can be obtained from groundnut or which comprises a portion or a sequence of a protein obtainable from groundnut. In a particular embodiment, the protein is selected from seed storage proteins. Preferably, the protein is selected from Ara h 1, Ara h 2, Ara h 3, Ara h 4, Ara h 5, Ara h 6, Ara h 7, Ara h 8 and Ara h 9 from Arachis hypogaea. In a most preferred embodiment, the protein derived from groundnut comprises at least Ara h 1, Ara h 2 or Ara h 3 or their isoforms. The amino acid sequences of Ara h 1, Ara h 2 and Ara h 3 are known to the skilled person. As an illustration, the Genbank accession numbers of Ara h 1 protein, two Ara h 2 isoforms and two Ara h 3 isoforms are, respectively, AAL27476, AAM78596, AAN77576, AAT39430 and AAC63045. These proteins can be obtained from a groundnut extract or produced by a recombinant organism, such as genetically modified bacteria, yeasts or by any other methods known by the man skilled in the art. These proteins can be used in combination or separately. It should be understood that the term "protein derived from groundnut" also includes fragments or variants of the above antigens, such as epitope-containing fragments, or proteins obtained from groundnut and subsequently enzymatically, chemically, mechanically or thermally modified.

In a particular embodiment, the groundnut allergen composition comprises one or more proteins derived from groundnut.

In another embodiment, the groundnut allergen composition comprises one or more proteins derived from groundnut selected from Ara h 1, Ara h 2 and Ara h 3, optionally in combination with others proteins derived from groundnut.

In another embodiment, the groundnut allergen composition comprises a groundnut extract as a source of proteins derived from groundnut.

A groundnut extract designates any preparation (lysate, filtrate, homogenate etc.) obtained from groundnut. The groundnut extract can be used directly or groundnut allergens can be at least partially purified from this extract. This purification process can involve filtration, centrifugation, precipitation or any other techniques known by the skilled person. Preferably, proteins derived from groundnut and administered to the subject are at least partially purified.

In one embodiment, the groundnut allergen composition is in a liquid form, such as a solution or a dispersion of particles. In that case, effective epicutaneous administration is ensured by migration of the allergen from the liquid phase of the allergen composition to the skin in order to allow the allergen to penetrate into the stratum corneum of the epidermis. In a particular embodiment, the migration of the allergen from the liquid phase of the allergen composition is ensured by diffusion of the allergen through the condensation formed within the hermetically closed chamber, e.g. as a result of perspiration.

In another embodiment, the groundnut allergen composition is in a dry form, in particular in a particulate form, obtained, for example, by lyophilisation. The present invention indeed shows that an efficient tolerance to groundnut can be achieved using a groundnut allergen preparation in a solid (e.g., dry) form. The use of proteins in particulate form is advantageous. Indeed, such particulate allergens may be directly attached to the backing of the device, thereby avoiding any chemical interaction or any reaction which might disturb the immunogenicity of these proteins. Moreover, the use of the particles allows preserving the substance in a suitable packaging, such that there is no longer any need to carry out an extemporaneous preparation. In this case, the epicutaneous administration of groundnut allergens held on the backing of the patch may be ensured by dissolution of these allergens in the condensation formed within the hermetically closed chamber.

In each embodiment, the condensation present within the hermetically closed chamber may come from condensed perspiration secreted by skin.

As used herein, the term "perspiration", "sweating" or "transpiration" means the production of a fluid that is excreted by the sweat glands in the skin of mammals. This fluid contains mainly water but also various dissolved minerals and trace elements. In the present invention, perspiration secreted by the skin evaporates and condenses within the hermetically closed chamber.

The term "condensation" refers, in this specification, to the change of the physical state of matter from gaseous phase into liquid phase, particularly the change of evaporated perspiration into liquid phase. The condensation formed by the perspiration within the chamber following application of the patch device to the skin causes or enhances removal and epicutaneous delivery of the allergens. In fact, the allergens may be dissolved in the water contained in the condensed perspiration and thereafter delivered to the subject via the epicutaneous route.

The allergen composition may further comprise additional components, such as adjuvants.

In a preferred embodiment, however, the groundnut allergen composition used in the present invention is formulated without any adjuvant. The invention indeed surprisingly shows that groundnut immunotherapy can be accomplished through the epicutaneous route without the need for additional adjuvant. The invention further shows that such a tolerance may be induced even without modifying the skin surface (e.g., with no perforation).

Although not preferred, the groundnut allergen composition used in the present invention may comprise or be applied with an adjuvant. Within the context of this invention, an adjuvant designates any substance that acts to activate, accelerate, prolong, or enhance antigen-specific immune responses when used in combination with specific antigen. Adjuvant compounds that can be used in combination with groundnut allergens include mineral salts, such as calcium phosphate, aluminium phosphate, and aluminium hydroxide; immunostimulatory DNA or RNA, such as CpG oligonucleotides; proteins, such as antibodies or Toll-like receptor binding proteins; saponins e.g. QS21; cytokines; muramyl dipeptide derivatives; LPS; MPL and derivatives including 3D-MPL; GM-CSF (Granulocyte-macrophage colony-stimulating factor); imiquimod; colloidal particles; complete or incomplete Freund's adjuvant; Ribi's adjuvant or bacterial toxin e.g. cholera toxin or enterotoxin (LT). In a particular embodiment, the groundnut allergen composition is formulated with enterotoxin.

The skin patch device used in the method of the invention comprises a backing, the periphery of said backing being adapted to create with the skin a hermetically closed chamber. This backing bears on its skin facing side within the chamber the groundnut allergen composition used to induce an immune reaction.

The term "hermetically closed chamber" as used in the present specification, means that the backing of the patch is moisture impervious and that the periphery of this backing constitutes an occlusive barrier thereby defining an enclosed space. The moisture impermeability of this chamber is required to allow allergens being removed from the backing, e.g., by dissolution or extraction, through the effect of moisture within said chamber and thereafter being delivered to the subject. The effectiveness of the patch is greatly conditioned by the creation of this liquid phase, in which the allergen is in solution or in suspension, thus promoting its passage through the pores.

The term "moisture" as used in the present specification, means the presence of water or other liquid in either the liquid or vapour phase.

Preferably, the periphery of the backing has adhesive properties and forms an airtight joint to create with the skin a hermetically closed chamber.

In a particular embodiment, the groundnut allergens are maintained on the backing by means of electrostatic and/or Van der Waals forces. This embodiment is particularly suited where the groundnut allergens are in solid form (e.g., particles), although it may also be used, indirectly, where the allergens are in a liquid form.

Within the context of the present invention, the term "electrostatic force" generally designates any non-covalent force involving electric charges. The term Van der Waals forces designates non-covalent forces created between the surface of the backing and the solid allergen, and may be of three kinds: permanent dipoles forces, induced dipoles forces, and London-Van der Waals forces. Electrostatic forces and Van der Waals forces may act separately or together.

In this respect, in a preferred embodiment, the patch device comprises an electrostatic backing. As used herein, the expression "electrostatic backing" denotes any backing made of a material capable of accumulating electrostatic charges and/or generating Van der Waals forces, for example, by rubbing, heating or ionization, and of conserving such charges. The electrostatic backing typically includes a surface with space charges, which may be dispersed uniformly or not. The charges that appear on one side or the other of the surface of the backing may be positive or negative, depending on the material constituting said backing, and on the method used to create the charges. In all cases, the positive or negative charges distributed over the surface of the backing cause forces of attraction on conducting or non-conducting materials, thereby allowing to maintain the allergen. The particles also may be ionized, thereby causing the same type of electrostatic forces of attraction between the particles and the backing.

Examples of materials suitable to provide electrostatic backings are glass or a polymer chosen from the group comprising cellulose plastics (CA, CP), polyethylene (PE), polyethylen terephtalate (PET), polyvinyl chlorides (PVCs), polypropylenes, polystyrenes, polycarbonates, polyacrylics, in particular poly(methyl methacrylate) (PMMA) and fluoropolymers (PTFE for example). The foregoing list is in no way limiting.

The back of the backing may be covered with a label which may be peeled off just before application. This label makes it possible, for instance, to store the groundnut allergen in the dark when the backing is at least partially translucent.

The intensity of the force between a surface and a particle can be enhanced or lowered by the presence of a thin water film due to the presence of moisture. Generally, the patch is made and kept in a dry place. The moisture shall be low enough to allow the active ingredient to be conserved. The moisture rate can be regulated in order to get the maximum adhesion forces.

As discussed above, the use of an electrostatic backing is particularly advantageous where the allergen is in a dry form, e.g., in the form of particles. Furthermore, the particle size may be adjusted by the skilled person to improve the efficiency of electrostatic and/or Van der Waals forces, to maintain particles on the support. Preferably, the size of the particles is in the range of 1 to 60 micrometers.

In a specific embodiment, the patch comprises a polymeric or metal or metal coated polymeric backing and the particles of groundnut allergens are maintained on the backing essentially by means of Van der Waals forces. Preferably, to maintain particles on the support by Van der Waals forces, the average size of the particles is lower than 60 micrometers.

In another embodiment, the groundnut allergens are maintained on the backing by means of an adhesive coating on the backing. The backing can be completely covered with adhesive material or only in part. Different occlusive backings can be used such as polyethylene or PET films coated with aluminium, or PE, PVC, or PET foams with an adhesive layer (acrylic, silicone, etc.).

Groundnut allergen composition in particulate form can be loaded on the backing by means of a spray-drying process, such as an electrospray process as described in the patent application no. WO2009/095591. An electrospray device uses high voltage to disperse a liquid in the fine aerosol. Allergens dissolved in a solvent are then pulverized on the patch backing where the solvent evaporates, leaving allergens in particle form. The solvent may be, for instance, water or ethanol, according to the desired evaporation time. Other solvents may be chosen by the skilled person. This type of process to apply substances on patch backing allows nano-sized and mono-sized particles with a regular and uniform repartition of particles on the backing. This technique is adapted to any type of patch such as patch with backing comprising insulating polymer, doped polymer or polymer recovered with conductive layer. Preferably, the backing comprises a conductive material.

In another embodiment, the periphery of the backing is covered with a dry hydrophilic polymer, capable of forming an adhesive hydrogel film by contact with the moistured skin (as described in the patent application no. WO2009/050403). In this embodiment, the skin has to be moistured before the application of the patch. When the hydrogel comes into contact with the moistured skin, the polymer particles absorb the liquid and become adhesive, thereby creating a hermetically closed chamber when the patch is applied on the skin. Examples of such hydrogels include polyvinylpyrolidone, polyacrylate of Na, copolymer ether methyl vinyl and maleic anhydride.

In another particular embodiment, the liquid groundnut allergen composition is held on the support of the patch in a reservoir of absorbent material. The composition may consist in an allergen solution or in a dispersion of the allergens, for example in glycerine. The adsorbent material can be made, for example, of cellulose acetate.

The backing may be rigid or flexible, may or may not be hydrophilic, and may or may not be translucent, depending on the constituent material. In the case of glass, the support may be made break-resistant by bonding a sheet of plastic to the glass.

In one embodiment, the backing of the patch contains a transparent zone allowing directly observing and controlling the inflammatory reaction, without necessarily having to remove the patch. Suitable transparent materials include polyethylene film, polyester (polyethylene-terephtalate) film, polycarbonate and every transparent or translucent biocompatible film or material.

In a particular embodiment, the portion of the backing bearing the allergen is not in direct contact with the skin. In this embodiment, the height of the chamber defined by the backing, the periphery of the backing and the skin is in the range of 0.1 mm to 1 mm.

The method of the invention typically involves the repeated administration of one or more groundnut allergens to the subject as disclosed above, leading to a progressive increase in tolerance in the subject.

The specific dose of allergen as well as the number of applications and duration of contact can be adapted by the skilled artisan, depending on the subject, the nature of the allergen preparation, the type of patch device used, etc.

Generally, the method comprises the application of at least two patch devices as disclosed above, preferably at least 3, 5, 10 or 15, over a period of time comprised between a week and years. The treatment may be stopped at any time, e.g., once an effective tolerance has been established.

In one embodiment, the method of the invention involves the repeated application of 1 to 4 patches per day, at least once a week, over a period of 1 month to several years. In a preferred embodiment, the method of the invention involves the application of 1 patch per day, every day or at least once a week, over a period of 1 month to several years. The duration of contact of the patch with the skin for each application is in the range of about 1 to 50 hours, typically about 12 to 48 hours, e.g., around 48 hours, 24 hours or 8 hours.

In a particular treatment regimen, the device is applied for 24 hours over a two-week period (e.g., continuous regimen with 14 devices per subject), which may subsequently be continued with broader treatment intervals.

In another particular treatment regimen, the device is applied for 48 hours every other day over a two-week period (e.g., regimen with 7 devices per subject), which may subsequently be continued with broader treatment intervals.

The amount of groundnut allergens on each patch is typically in the range of 0.1 to 1000 $\mu g/cm^2$ of patch surface, preferably in the range of 20 to 500 $\mu g/cm^2$ of patch surface, more preferably in the range of 20 to 200 $\mu g/cm^2$ of patch surface. The patch surface is in the range of 1 $cm^2$ to 10 $cm^2$, preferably in the range of 1 $cm^2$ to 5 $cm^2$.

For application, the patch devices may be applied directly to the skin, without any pre-treatment, preferably on a hairless part of the body. Alternatively, the skin may be treated prior to application of the device, to disrupt the stratum corneum, to remove hairs or simply to cause hydration of the skin, at the site of contact with the patch device. To efficiently increase the tolerance of the subject to groundnuts, groundnut allergens are preferably administered in a dose sufficient to induce an immune reaction in the subject.

This immune reaction can involve an inflammatory reaction leading to a cascade of biochemical events involving the local vascular system and the immune system. Inflammatory reaction is either moderate in the form of erythema (first clinical element of the inflammatory reaction), or in the form of a papula also indicating the presence of local edema (another component of the inflammatory reaction). The inflammatory reaction induced by the application of groundnut allergens via the epicutaneous route can be visible or non visible to the unaided eye.

As disclosed in the experimental section, the method of the invention results in a reduction of specific IgE levels and an increase in some specific IgG levels, in particular in IgG4 levels, leading to a progressive increase in tolerance to groundnut. The term "specific Ig" refers herein to immunoglobulins which are specific to at least one allergen to which the subject is allergic. In a preferred embodiment, these immunoglobulins are specific to at least one protein derived from groundnut, especially Ara h 1, Ara h 2 or Ara h 3 or their isoforms.

The method of the invention also leads to an immune deviation from a dominant Th2 profile to a more balanced Th1/Th2 profile. In other words, the method of the invention causes a raising of a Th1 response to the proteins administered. Th1 and Th2 cells are two types of CD4+ helper T-cells which differ in their pattern of cytokines production. Th1 cells produce IFN-γ, IL-2 and TNF-β and are involved in cell-mediated immune responses that are beneficial in host-defence against intracellular pathogens and malignant cells, but detrimental in mediating autoimmunity. Th2 cells secrete IL-4, IL-5, IL-9, IL-10 and IL-13, which increase antibody responses, including IgE production, and protect against parasitic infestations but can also cause allergy and asthma. Th1 and Th2 responses are mutually antagonistic, such that they normally exist in equilibrium and cross-regulate each other. In an allergic subject, the balance Th1/Th2 is altered and the Th2 profile is predominant. An immune deviation from dominant Th2 profile to a more balanced Th1/Th2 profile means a deviation from an allergic state to a tolerant state. This deviation, mediated by an increase of Treg cells, can be evaluated by any method known by the skilled person, such as a decrease in ratio IgG1/IgG4 or the analysis of cytokine production.

The examples presented also show the epicutaneous method of this invention reduces airway hyper-responsiveness and lung eosinophilia. The method also prevents mastocyte degranulation in treated subjects. The method is thus potent for immunotherapy of allergic patients. Moreover, the method is not only at least as potent as subcutaneous injections, but it avoids risks associated with injections, and is much more controllable and comfortable during the whole treatment phase.

In a preferred embodiment, the method of the invention is free of systemic effects. An inflammatory reaction is likely to be observed on the skin of the subject only at the site of the epicutaneous administration or in the direct periphery of this site. This inflammatory reaction can be modulated by the dose of allergen laid on the backing.

The present invention also provides a skin patch device, as described above, comprising a backing, the periphery of said backing being adapted to create with the skin a hermetically closed chamber, wherein the backing bears on its skin facing side within the chamber one or more groundnut allergens, as described in the present specification, in a dose sufficient to induce an immune reaction in the skin of a subject following application of the patch device to the skin, said one or more allergens being removed from the backing following application of the patch device to the skin and thereafter delivered to the subject via the epicutaneous route.

The present invention also relates to the use of a skin patch device as described above, in the manufacture of a composition for increasing tolerance to groundnut in a subject allergic to groundnut.

The present invention also relates to the use of a skin patch device as described above, in the manufacture of a composition for increasing a Th1-type immune response to groundnut in a subject allergic to groundnut.

The present invention also relates to a patch kit comprising a plurality of patches as described above, the patches of the kit containing the same or a different amount of groundnut allergen. Also, the allergen composition used on the patches of the kit can be the same or different. For example, different groundnut proteins can be used, with or without adjuvant. Preferably, the same composition is used over the course of the desensitization treatment.

The following examples are given for purposes of illustration and not by way of limitation.

EXAMPLES

A—Study 1
A1. Methods
Animals and Protein Extracts

Four-week-old female BALB/c mice purchased from Charles River Laboratories (France) were sensitized to peanut proteins. The use of BALB/c mice as murine model of sensitization to peanut proteins was described in Adel-Patient et al., *Peanut-and cow's milk-specific IgE, Th2 cells and local anaphylactic reaction are induced in Balb/c mice orally sensitized with cholera toxin*, 60(5) ALLERGY 658, 658-64 (2005). This model should reproduce the IgE fine specificity and the symptoms as observed in allergic humans upon challenge. All experiments were performed according to European Community rules of animal care.

Peanut extract was prepared by mixing peanut powder (Allergon, Sweden) in 20 mM phosphate buffer pH 7.4 containing 1 M NaCl during 4 hours at room temperature. After centrifugation, supernatant was kept as peanut protein extract (PPE). PPE was then dialysed and protein content was quantified by BCA assay and analysed by SDS PAGE. Endotoxin levels were below 0.06 ng/ml (E-toxate kit, Sigma, France).

Protocol of Sensitization

Eight BALB/c mice received 1 mg of homogenized PPE mixed with 10 µg of Cholera Toxin (CT) on days 1, 6, 12, 18, 24, 30 by means of intra-gastric gavages. Sera were collected from the retro-orbital venous plexus on days 0, 18 and 43, centrifuged, and the samples were stored at −20° C. until further assays. Naïve mice were bled on the same days (n=8). Sensitization was monitored by biological parameters as defined above.

Protocol of Desensitization

Desensitization was perfomed once a week during 8 and 16 weeks via epicutaneous (EP) route as follow:

Mice were anaesthetized intraperitoneally with ketamine and xylazine and shaved with an electric clipper and depilatory cream. The day after, skin patch devices with a backing bearing 100 µg of PPE in dry form, the periphery of said backing being adapted to create with the skin of the mouse a hermetically closed chamber, were placed on the back of the mouse and maintained by a bandage for 48 hours.

Allergen Challenge and Quantification of Histamine Release

Mice were fasted overnight and challenged with intragastric gavage with PPE of 10 mg per mouse divided into 2 doses at 30 minutes intervals. Naïve mice were challenged in the same manner. To determine plasma histamine levels, blood was collected 30 minutes after the second intragastric gavage challenge and stored at −20° C. until analyzed. Histamine levels were determined by using an enzyme immuno-assay kit (SPI-BIO, France) as described by the manufacturer.

Quantification of Specific IgE, IgG1, IgG2a

Blood samples were collected from retro-orbital venous plexus before and during immunotherapy and the plasma were stored at −30° C. until further analyses.

A quantitative ELISA, validated using ICH guidelines, was used for specific IgE, IgG1 and IgG2a. Briefly, microtiter plates were coated with PPE act at a concentration of 10 µg/ml. Serial dilutions of 100 µl of each serum were dispensed per well and incubated for 24 h at 4° C. An anti-mouse IgG1 or IgG2a antibody labelled with phosphatase alkaline (Serotec, England) was used as a tracer. Reagent (pNPP) (Sigma, France) was used as an enzyme substrate. Specific IgE, IgG1 and IgG2a were quantified by comparison with concentration-response curves obtained with a total IgE, IgG1 or IgG2a assay performed under identical conditions using a solid phase coated with an anti-mouse IgE, IgG or IgG2a antibody (Serotec, England) instead of peanut proteins, which is complementary to tracers. Mouse immunoglobulin standards were obtained from Serotec.

IgA Assay

Specific IgA were determined on sera samples. Sera (1/50) diluted in PBS buffer containing 0.1% BSA were incubated on plates coated with PPE at 10 $\mu g \cdot ml^{-1}$. Specific IgA were detected using goat anti-mouse IgA (Southern Biotechnology Associated, USA) labelled with phosphatase alkaline and detected as above. Results are reported as absorbance units at 405 nm.

Cytokine Production

After the last blood sampling, mice were killed by vertebral dislocation and spleens were harvested under sterile conditions. Cell culture were performed in the presence of PPE (2.5-250 $\mu g \cdot l^{-1}$), PBS (negative control) or concanavalin A (1 $\mu g \cdot ml^{-1}$, positive control). IL-4, IL-5, IL-10, IFN$\gamma$ and TGF$\beta$ were assayed using CytoSet™ kits (BioSource International Europe, Belgium) according to the manufacturer's instructions.

Delayed-type Hypersensitivity Response (DTH)

To elicit a DTH response, mice were challenged after the last oral immunization by an injection of 100 µg peanut protein in PBS into the hind footpad. PBS was injected in the other footpad. Net swelling of the both footpad was measured using a microcalliper 24 h after challenge and was compared each other.

Statistical Analysis

The Graph Pad Software (San Diego, USA) was used for statistical analysis. Data were analysed using analysis of variance (ANOVA) and Dunnett's test when comparing treated mice with controls, or using ANOVA and Tukey's test when comparing all the groups with each other.

A2. Results
Preliminary Remarks

The understanding of the immune system in mice and in human and the study of their similarities and differences in mechanisms such as Th1 and Th2 responses are still going on. In order to assess the model which has been developed as a proof of concept of epicutaneous immunotherapy, some elements about the main allergic biomarkers and their interpretation in human and mouse are provided, especially concerning the balance Th1/Th2.

Degranulation of mast cells: In human, IgE is the only immunoglobulin isotype that directly triggers the degranulation of mast cells and subsequent manifestation of anaphylaxis, whereas in mouse, degranulation of mast cells is triggered by IgG1 together with IgE.

Production of IgG antibodies: In human, the production of IgG antibodies, primarily the IgG4 subtype, can antagonize and 'block' the allergic inflammation cascade resulting from antigen recognition by IgE. In mouse, equivalent antibodies are not described and the switch from Th2 to Th1 profile consists of the increase of IgG2a antibody.

In human, the production of IgE and IgG4 is stimulated in Th2 cells whereas the production of IgG1 and IgG3 is stimulated in Th1 cells.

In mouse, the production of IgE and IgG1 is stimulated in Th2 cells whereas the production of IgG2a and IgG3 is stimulated in Th1 cells.

To sum up, in murine model, the efficacy of immunotherapy was essentially assessed by the increase of specific IgG2a.

1. Validation of Sensitisation 1.1 Specific IgE, IgG1, IgG2a During Sensitization PPE specific antibodies induced in BALB/c mice after administration of PPE by gavage were analyzed. Peanut-sensitization in mice was marked by a production of specific IgE and IgG1 as shown in FIG. 1. IgG2a was also produced but at to a lesser extent than specific IgG1. No specific antibodies could be detected in naïve mice.

1.2 Cytokines Secreted After in vitro Reactivation of Splenocytes

Figure 2:
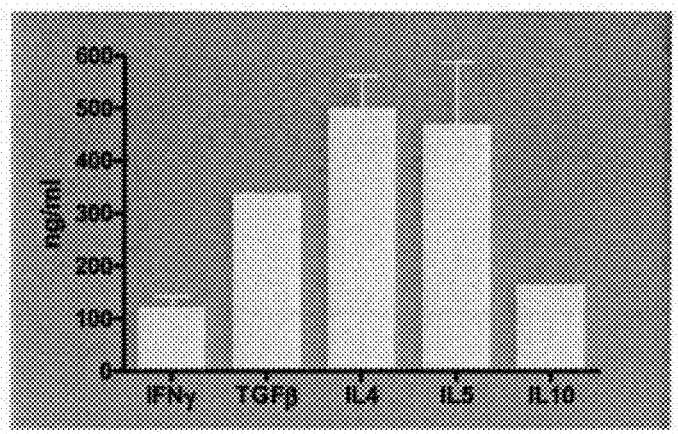
FIG. 2 is a graph that shows cytokines secreted by reactivated splenocytes from orally PPE-sensitized mice. Spleen cells from orally-sensitized BALB/c mice were isolated and reactivated ex vivo with PPE for 60 h. Cytokines were quantified on supernatant by an enzyme immunoassay.

Splenocytes from mice sensitized with CT plus PPE secreted high quantities of allergen-specific IL-4 and IL-5, and small amounts of IL-10, IFNγ and TGFβ (FIG. 2). No cytokine was found in control mice. These results demonstrated that the PPE-specific Th2 response was induced in BALB/c mice receiving peanut proteins by means of gavage.

1.3 Histamine Levels After Oral Challenge

Figure 3:
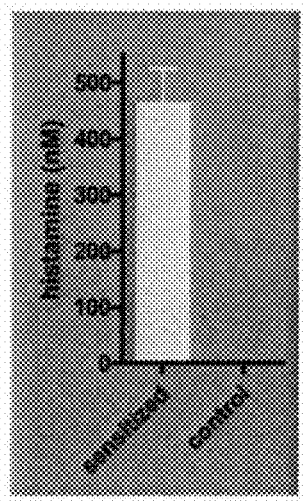
FIG. 3 is a graph that shows histamine levels in plasma samples obtained from sensitized and control mice after oral challenge. Histamine was assayed as competitive EIA.

Because histamine increased levels reflect mast cell degranulation and is one of the major mediators of anaphylactic reaction, histamine was assayed in plasma after oral challenge. Histamine was detectable only in plasma sample from sensitized mice (FIG. 3).

1.4 Delayed Type Hypersensitivity (DTH)

Figure 4:
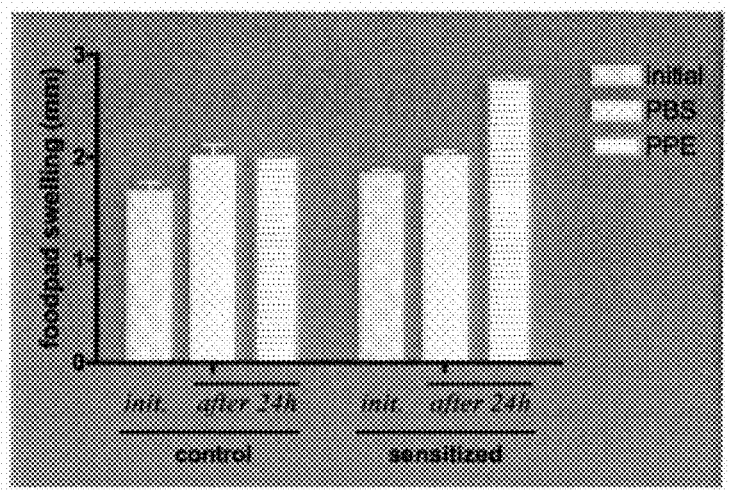
FIG. 4 is a graph that shows DTH responses measured 24 h after single peanut protein challenge in the footpad and expressed as mean increment of footpad swelling (SEM). Init.: measure of the footpad before the injection of PPE or PBS. PBS was injected in the right footpad and PPE on the other footpad. The swelling of each footpad was measured 24 h after injection.

To complete the previous results showing the sensitization of mice to peanut proteins, the DTH response was investigated. A footpad challenge was performed at the end of sensitization and demonstrated a swelling only for sensitized mice (FIG. 4). No DTH response was found in footpad treated with PBS.

2. Peanut Immunotherapy 2.1 Formulation for Immunotherapy

Figure 5:
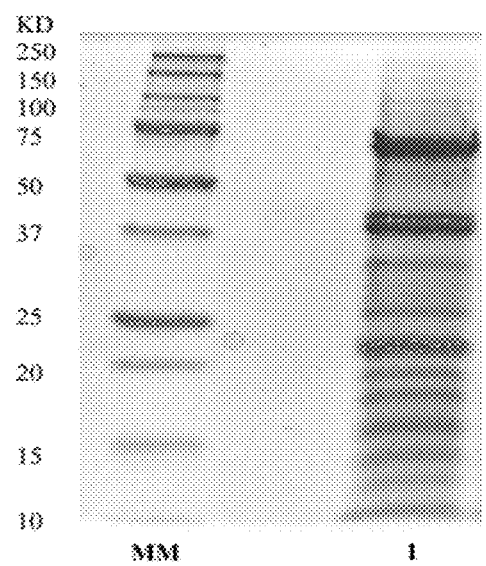
FIG. 5 shows the electrophorectic pattern (in denaturing and reducing conditions) of PPE formulation.

Protein content of the formulation used for immunotherapy was characterized by SDS-PAGE (FIG. 5).

2.2 Specific IgE, IgG1, IgG2a During Immunotherapy

Figure 6:
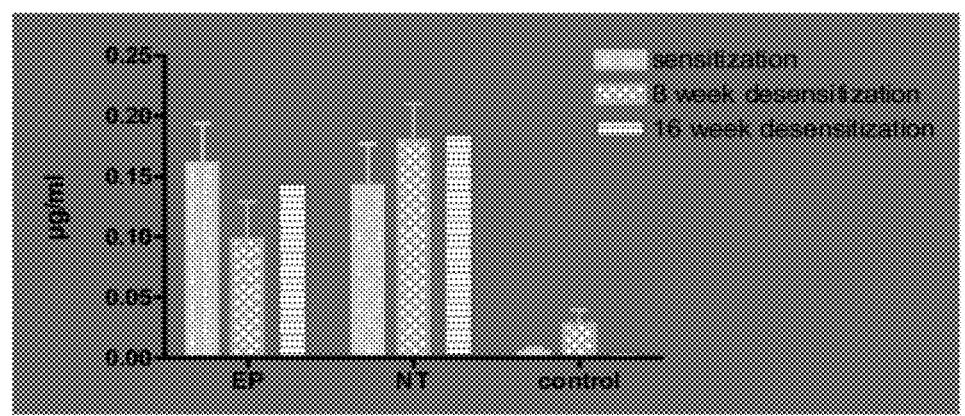
FIG. 6 shows a graph representing the concentration of specific IgE in control mice and sensitized mice desensitized by epicutaneous route (EP) or non treated (NT). Results are expressed as mean in $\mu g \cdot ml^{-1}$ +/−SD.

IgE and IgG1: Peanut sensitization was particularly characterized by a production of specific IgE and IgG1. During immunotherapy, the evolution of specific antibodies was monitored. As shown in FIG. 6, the production of specific IgE was stabilized during 8 and 16 weeks of desensitization. The decrease of specific IgE is a long term process which can be observed only after some months. Furthermore, during the immunotherapy, no modification of specific IgG1 was observed (data not shown).

Figure 7:
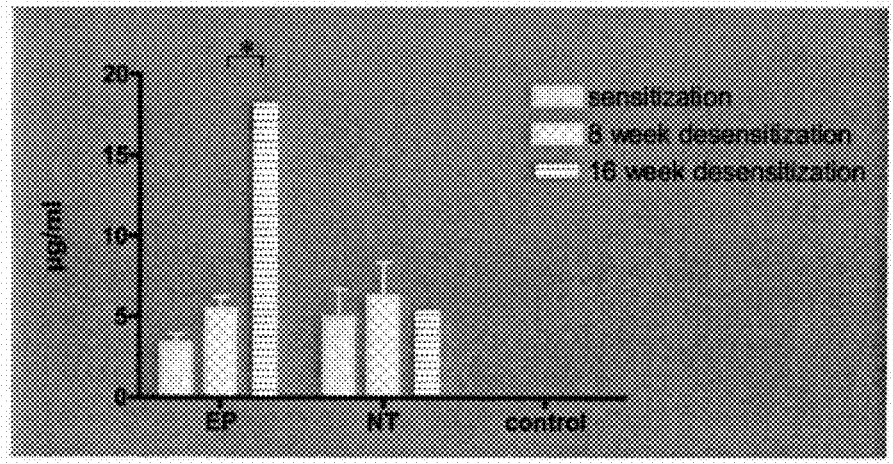
FIG. 7 shows a graph representing the concentration of specific IgG2a in control mice and sensitized mice desensitized by epicutaneous route (EP) or non treated (NT). Results are expressed as mean in $\mu g \cdot ml^{-1}$ +/−SD.

IgG2a: specific IgG2a significantly increased for treated mice after 8 weeks and 16 weeks of desensitization (FIG. 7).

Figure 8:
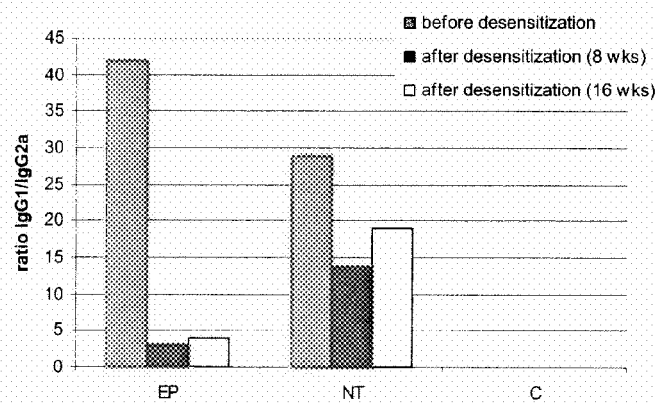
FIG. 8 shows a graph representing the ratio IgG1/IgG2a for the desensitization group (EP), non treated mice (NT) and controls (C). Results are shown after 8 weeks and 16 weeks of desensitization.

To confirm the immune deviation from a dominant Th2 profile to a balanced Th2/Th1 profile, the ratio IgG1/IgG2a was evaluated for each group: EP desensitization, NT and control (FIG. 8). The ratio IgG1/IgG2a decreased only for treated mice showing a boosting of Th1 profile in order to obtain a more balanced Th2/Th1 profile.

2.3 Histamine

Figure 9:
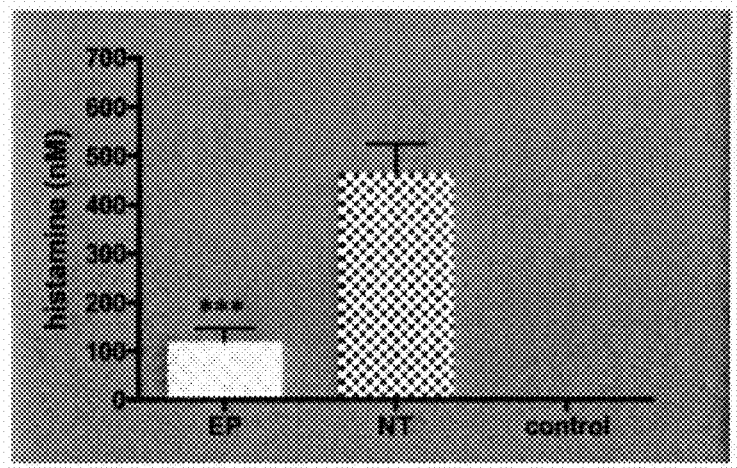
FIG. 9 shows a graph representing the concentration of histamine in plasma samples after oral challenge from control mice and sensitized mice desensitized by epicutaneous route (EP) or non treated (NT). Results are expressed as mean in nM +/−SD. * $p<0.05$,  $p<0.001$, * $p<0.001$.

Histamine is one of the major mediators of anaphylactic reaction. Histamine was assayed in plasma samples collected 30 minutes after oral challenges as a marker of the degranulation of mast cells. After 16 weeks of desensitization, the histamine release was quantified for mice of each group (treated or not) (FIG. 9). Mice treated epicutaneously with PPE showed a significantly lower release of histamine. This result confirmed an improvement of the allergic status of mice.

2.4 Specific IgA During Immunotherapy

Figure 10:
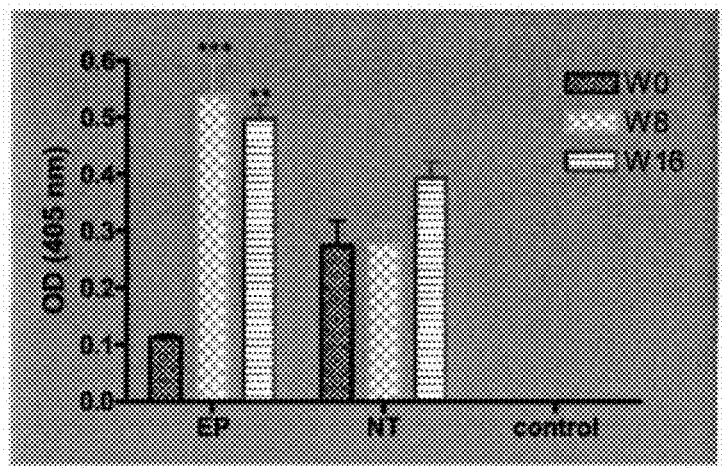
FIG. 10 shows a graph representing the concentration of peanut specific IgA in sera samples in mice treated (EP) with PPE formulation or non treated (NT) and control. Results on sensitized mice (W0) and after 8 (W8) and 16 weeks (W16) of desensitization are expressed in optical density (OD) at 450 nm. * $p<0.05$,  $p<0.001$, * $p<0.001$.

Titration of specific IgA was performed on serum samples after 8 weeks of desensitization (FIG. 10). Specific IgA were significantly increased in mice treated by epicutaneous route with PPE after 8 weeks of desensitization. No modification was observed in non treated mice. Specific IgA was not detectable in control mice.

Specific IgA is described as having a similar action as IgG4 during immunotherapy. Its immunomodulatory effect could lead to IL-10 production and TGFβ expression. Francis et al., *Grass pollen immunotherapy: IL-10 induction and suppression of late responses precedes IgG4 inhibitory antibody activity*, 121(5) J. ALLERGY CLIN. IMMUNOL. 1120, 1120-1125 (2008).

A3. Conclusions

Epicutaneous route displays potent and original way of desensitization on peanut-sensitized mice.

Epicutaneous desensitization led to an immune deviation from a dominant Th2 profile to a rebalanced Th2/Th1 profile and increased specific IgA. As a marker of allergenicity (degranulation of mast cells), histamine release was decreased in mice treated by epicutaneous route.

B—Study 2

Study 1 has been extended to a much larger number of animals, as disclosed below.

B1. Materials And Methods

Figure 11:
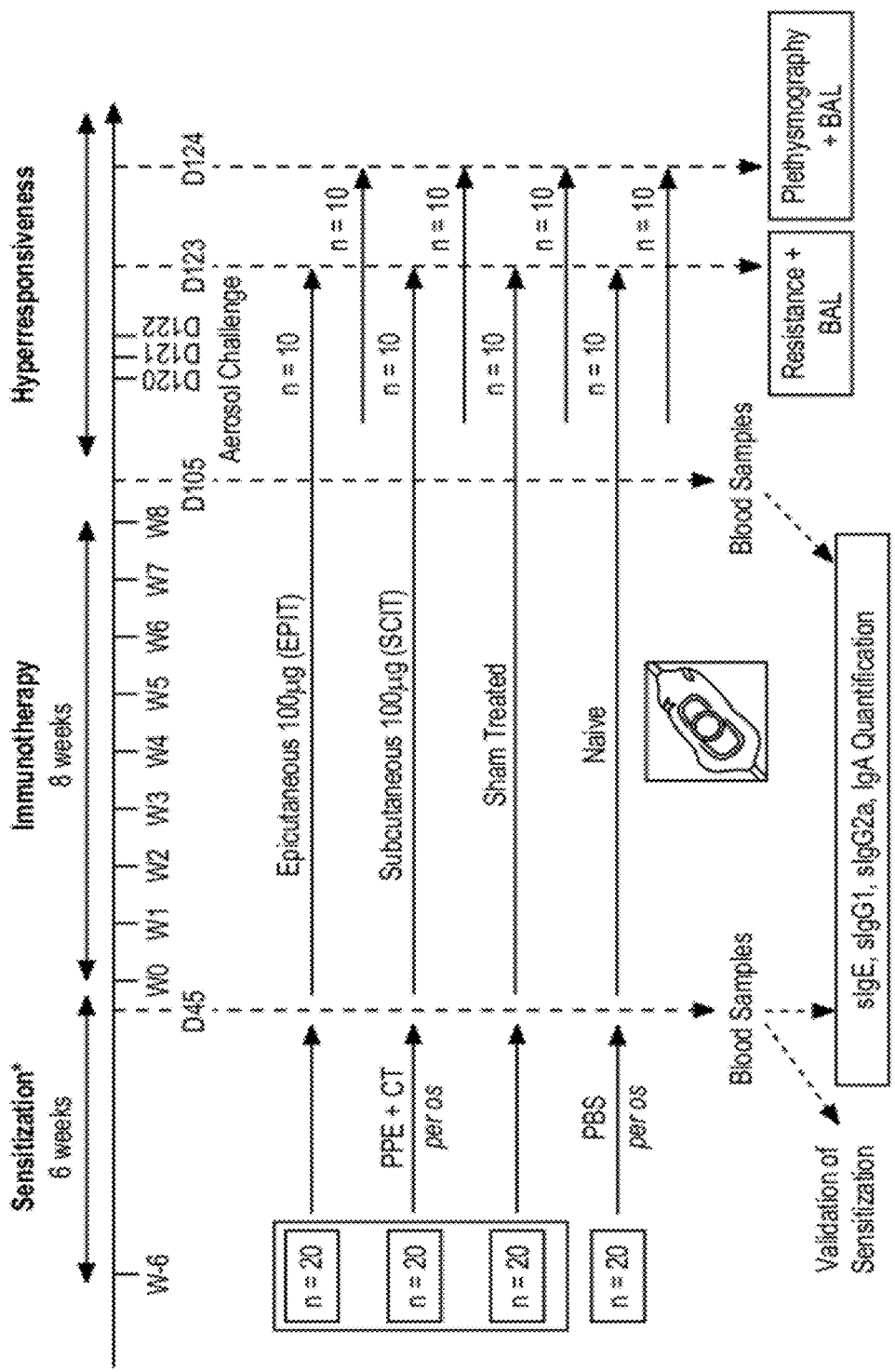
FIG. 11: Study design for peanut immunotherapy. The first phase was sensitization of mice to peanut proteins. After validation of the sensitization, immunotherapy was performed by epicutaneous (EPIT) or subcutaneous (SCIT) routes during 8 weeks.

Study Design (FIG. 11)

After a phase of sensitization validated by an increase in the specific IgE (sIgE), mice were divided into 3 groups of 20 animals and received epicutaneous immunotherapy (EPIT), sub-cutaneous immunotherapy (SCIT) or a sham treatment during 8 weeks. Twenty (20) naïve mice were also included.

Ten days after the end of the treatment, groups were split by half. The first half-groups were submitted to measurement of histamine release in blood after a peanut oral challenge, then to evaluation of airway hyper-responsiveness (AHR) by plethysmography after 3 days of peanut aerosol challenge. The second half allowed evaluation of AHR by resistance-compliance technique (flexiVent®, SCIREQ, Montreal, Canada) after 3 days of aerosol challenge. In all animals, a broncho-alveolar lavage (BAL) was finally performed for cytological and immunological analyses.

Animals

Three-week-old (n=80) female BALB/c mice (Charles Rivers, Lyon, France) were purchased and housed under standard animal husbandry conditions. All experiments were performed according to the European Community rules on animal care, with permission 92-305 from the French Veterinary Services and with a positive evaluation of Ethical Committee (P2.LM.059.08, Paris-Descartes, Paris, France). Mice were acclimated for 1 week before immunization.

Skin preparations before EDS application, were all performed under general anesthesia by Ketamine (Imalgen 1000, Merial) (100 mg/kg body weight) and Xylazine (Rompun®, Bayer) (10 mg/kg body weight), BAL and respiratory tests under anesthesia by pentobarbital (Nembutal®, Sanofi Santé animale, CEVA) (50 mg/kg body weight) administered intraperitoneally, and venipuncture under isoflurane.

Immunization

Mice were sensitized to peanut (n=60) by means of 6 intra-gastric gavages, once a week during six weeks, with 200 µl of a solution containing 1 mg of homogenized peanut protein extract (PPE) mixed with 10 µg of Cholera Toxin (CT-Servibio, USA).

Sensitization was controlled by the production of specific IgE in blood 10 days after the last injection.

Naïve mice received 200 µl of phosphate-buffered saline (PBS) by oral administrations using the same scheme as sensitized mice.

Treatment

Epicutaneous Immunotherapy (EPIT)

Figure 12:
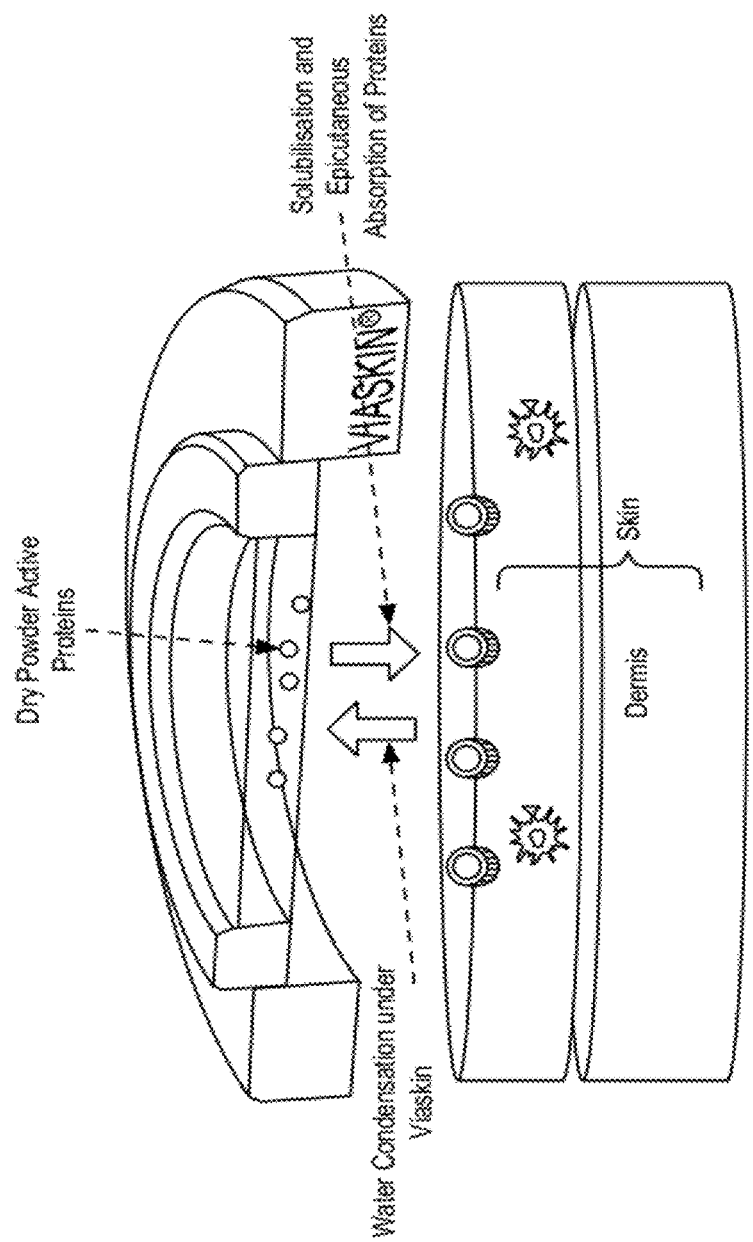
FIG. 12: VIASKIN® technology. Proteins are loaded in the central polyethylene membrane charged with electrostatic forces. The delivery system creates an occlusive chamber on the skin that generates moisture and releases proteins from the membrane. Proteins are then absorbed through the skin where they interact with epidermal immune cells.

EPIT was performed using an original epicutaneous delivery system (EDS) (Viaskin®, DBV Technologies, Paris France, FIG. 12) consisting of a central transparent plastic membrane (11 mm in diameter) of polyethylene electrically charged with electrostatic forces and an adhesive sheath of nonwoven film. Dry powder of PPE is maintained on the backing by electrostatic forces. An occlusive chamber is created on the skin that rapidly generates moisture and releases the allergen from its support. The allergen is then absorbed by the skin where it interacts with epidermal immune cells.

EDS with 100 µg of peanut protein extract (PPE) were applied for 48 h to the back of mice, once a week during 8 weeks. Twenty-four (24) hours before application, skin was shaved with an electric clipper and depilatory cream was applied. This technique does not modify the barrier properties of the skin. This was demonstrated in a previous experience by the absence of change in the trans-epithelial water loss (TEWL), as compared with hairless mice (6.45±1.22 vs. 6.63±1.49 g/h/m$^2$, ns).

Subcutaneous Immunotherapy (SCIT)

Once a week during 8 weeks, mice of the SCIT group received 200 µl of a homogeneous suspension of 100 µg of peanut injected subcutaneously between shoulders, as previously described. Lagranderie et al., *Mycobacterium bovis BCG killed by extended freeze-drying reduces airway hyper-responsiveness in 2 animal models,* 121(2) J. ALLERGY CLIN. IMMUNOL. 471, 471-78 (2008).

Sham and Naive Groups

The sham group received an empty EDS during immunotherapy, with the same design as for EPIT. No treatment was administered to the naive group.

Specific IgE, IgG1 and IgG2a in Blood

Blood was collected from retro-orbital venous plexus 10 days after sensitization (D45) and 10 days after treatment (D105).

Specific antibodies were quantified using a quantitative ELISA developed in-house according to the 2001 FDA guidelines. Briefly, microtiter plates were coated with 100 µl per well of 5 µg/ml peanut solution. Serial dilutions of 50 µl of each serum were dispensed per well and incubated for 24 h at +4° C. An anti-mouse IgE, IgG1 or IgG2a antibody labeled with phosphatase alkaline (Serotec, Oxford, England) was used as a tracer. Reagent (pNPP-Sigma, France) was used as an enzyme substrate. Specific IgE, IgG1 and IgG2a were quantified by comparison with concentration-response curves obtained with a total IgE, IgG1 or IgG2a assay performed under identical conditions using a solid phase coated with an anti-mouse IgE, IgG or IgG2a antibody (Serotec, Oxford, England). The cross-reactivity of secondary antibodies with immunoglobulin was less than 4% for all the antibodies and less than 0.1% for anti-IgG1 and anti-IgG2a antibodies against purified IgE.

Histamine Release in Blood

Histamine increase in blood reflects the percentage of mast cells degranulation. It was assayed in plasma samples 30 minutes after peanut oral challenge as a marker of anaphylactic reaction. Ten mice of each group were challenged at 30-minute intervals by 2 oral administrations of 10 mg PPE diluted in 200 µl of PBS. Histamine was assayed using a competitive enzyme immunoassay kit (SPI-BIO, Montigny-le-Bretonneux, France) in blood collected 30 minutes after the second oral challenge.

Airway Hyperresponsiveness (AHR)

Whole-body Plethysmography

Whole-body plethysmography was performed by placing mice into a closed chamber allowing recording of the pressure fluctuations during the breathing cycle. "Enhanced pause" (Penh) was calculated as previously described (Lagranderie M, JR et al), from the box pressure recorded during inspiration and expiration, and the timing comparison of early and late expiration. Penh corresponds to PEP/PIP, where PEP is peak expiratory pressure and PIP is peak inspiratory pressure. Mice were challenged with peanut by 30 minutes of aerosol (10 ml of 1% PPE in 0.9% NaCl) during 3 consecutive days. Pressures were measured 24 hours after the challenge and Penh values were calculated prior to and during 10 min after aerosol of various doses of methacholine (Sigma-Aldrich, Stonheim, Germany). For each mouse, Penh values were plotted against methacholine concentration (from 0 to 40 mg/ml) and the area under the curve (AUC) was calculated.

Resistance-compliance

Bronchial resistance and dynamic compliance were measured using the FlexiVent system (SCIREQ, Montreal, Quebec, Canada) after exposure to increasing doses of methacholine. Mice were anesthetized with intraperitoneal injections of pentobarbital (70 mg/kg). The trachea was exposed and a 19-gauge metal needle was inserted into the trachea. The needle was then connected to a computer-controlled small animal ventilator for quasi-sinusoidal ventilation of the mice with a tidal volume of 10 ml/kg at a frequency of 150 per minute and a positive end-expiratory pressure of 2 cmH$_2$O to achieve a mean lung volume close to that observed during spontaneous breathing. After measurement of baseline resistance and compliance, mice were challenged with increasing concentrations (0, 0.625, 1.25, 2.5, 5 and 10 mg/ml) of methacholine aerosol, generated with an in-line nebulizer and administered directly through the ventilator for 5 seconds. Resistance and compliance were measured using a "snapshot" protocol every 20 seconds for 2 minutes. The mean of these six values was determined for each methacholine concentration, unless the coefficient of determination of a measurement was smaller than 0.95. For each mouse, resistance values were plotted against methacholine concentration (from 0 to 10 mg/ml) and the AUC was calculated.

Cytokine Levels and Cell Composition in Blood and BAL Fluid

Blood samples for cytokine analyses were collected in anesthetized mice the day after AHR measurement. Eotaxin, interleukin (IL)-4, IL-5, IL-10, IL-13, IL-17, interferon (IFN)-γ and Tumor necrosis factor (TNF)-α were assayed with the Bio-Plex Cytokine Assay, according to the manufacturer's recommendations (Bio-Rad, Marnes La Coquette, France). Tumor growth factor (TGF)-β was analyzed by ELISA kit (R&D system, Minneapolis, USA).

In our assay, quantification thresholds were defined by the manufacter as 5.9 pg/ml (IL-4), 2.9 pg/ml (IL-5), 1.1 pg/ml (IL-10), 1.1 pg/ml (IL-13), 2.1 pg/ml (IL-17), 1.8 pg/ml (IFN-γ), 3.0 pg/ml (TNF-α), 5.8 pg/ml (eotaxin) and 12 pg/ml (TGF-β).

Cytokines and cells were measured in BAL fluids 24 and 48 hours after the last aerosol challenge. Cells were characterized using the cytospin slides stained with DiffQuick (Baxter Dade AG, Duedingen, Switzerland).

Statistical Analysis

The GraphPad Prism Software 5.0 (San Diego, Calif., USA) was used for statistical analysis (n=10-20 mice per group). Results are expressed as mean ± standard deviation (SD). Antibody responses as well as cell and cytokine data were analyzed using analysis of variance (ANOVA) and Tukey's test for intergroup comparisons. The raw data of Penh values were analyzed using the nonparametric Mann-Whitney U test. Penh and resistance data were also analyzed using the complete methacholine dose-response curve. For each mouse, Penh or resistance was plotted against methacholine concentration (from 0 to 40 mg/ml or from 0 to 10 mg/ml) and the AUC was calculated. Then, data were analyzed using analysis of variance (ANOVA) and Dunnett's test when comparing treated mice with controls, and using ANOVA and Tukey's test when comparing all the groups with each other.

B2. Results

Serological Response to Sensitization and Immunotherapy

Figure 13:
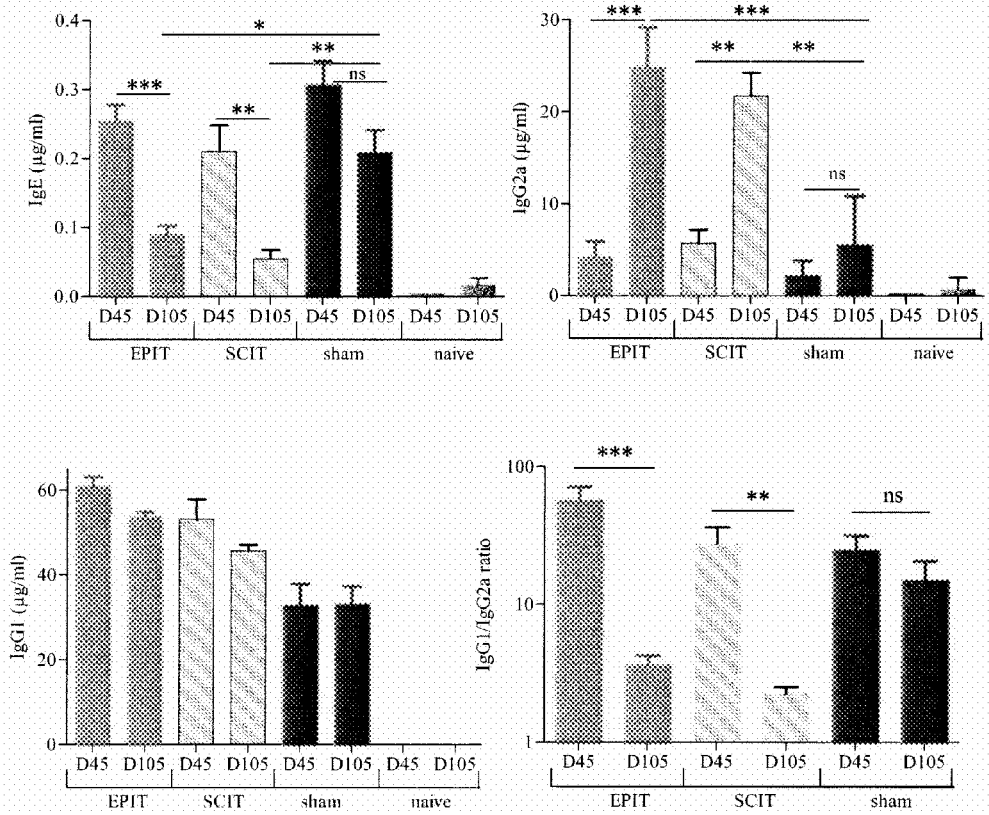
FIG. 13: Quantity of specific (a) IgE, (b) IgG2a and (c) IgG1, and (d) determination of the IgG1/IgG2a ratio expressed for each group. D45: values obtained at the end of sensitization phase (before immunotherapy). D105: values obtained at the end of immunotherapy. Groups were EPIT (epicutaneously treated mice), SCIT (subcutaneously treated mice), sham (sham treated mice) and naive (naive mice). Data are means ±SEM for each group of 20 mice, ns: non significant, * $p<0.05$,  $p<0.01$ and * $p<0.001$.

Specific sensitization against peanut protein was confirmed on day 45 by increased sIgE in the sera of EPIT, SCIT and sham mice, as compared with naïve mice (FIG. 13). Sensitization was not significantly different between groups. Ten days after the end of the treatment (D105), EPIT and SCIT had decreased sIgE ($p<0.001$) and increased sIgG2a (respectively $p<0.001$ and $p<0.01$ vs. sham). Treatment did not modify sIgG1, but dramatically decreased the sIgG1/sIgG2a ratio (respectively $p<0.001$ and $p<0.01$ vs. sham).

Figure 14:
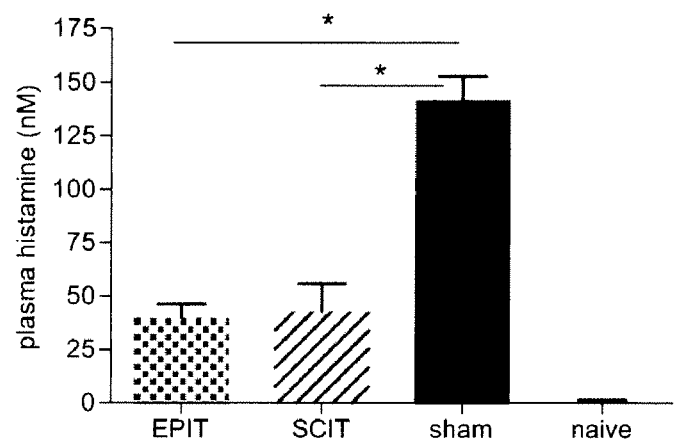
FIG. 14: Effect of immunotherapy (EPIT and SCIT) on plasma histamine levels. Blood was collected and plasma was obtained 30 minutes after challenge. Histamine levels were measured using an enzyme immunoassay kit. Data are means ±SEM for each group of 10 mice. * $p<0.05$.

General Reactivity: Histamine Release After Oral Challenge (FIG. 14)

Levels of histamine released in plasma sampled 30 min after oral challenge were high in sham (142±34 nM) and very low in naï mice (1.5±0.2 nM). It was significantly reduced by EPIT and SCIT ($p<0.05$ vs. sham).

AHR

Figure 15:
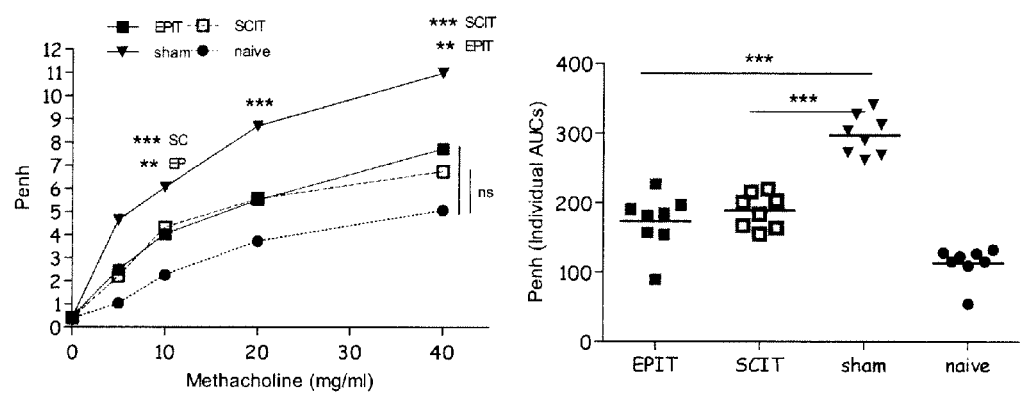
FIG. 15: AHR measured by whole body plethysmography 24 h after the last aerosol challenge to peanut. (a) Dose-response curves obtained for each group and (b) individual area under the curve (AUC) calculated from data of graph (a). Penh values were recorded after increasing doses of methacholine (from 0 to 40 $mg \cdot ml^{-1}$). EPIT: epicutaneous treated group, SCIT: subcutaneous treated group, sham treated group, naive group.  $p<0.01$ and * $p<0.001$.

Plethysmography (FIG. 15)

Dose-response curves to metacholine were significantly different between treated (EPIT, SCIT) and sham groups at methacholine dosages from 10 to 40 mg/ml. At the higher methacholine concentration (i.e. 40 mg/ml), sham mice responded to peanut challenge with marked AHR. As compared to sham, EPIT and SCIT showed significantly decreased Penh values (respectively $p<0.01$ and $p<0.001$), which did not differ significantly from naive. AUC values for Penh were also significantly lower with EPIT and SCIT than with sham ($p<0.001$), and did not differ from those of naive mice.

Figure 16:
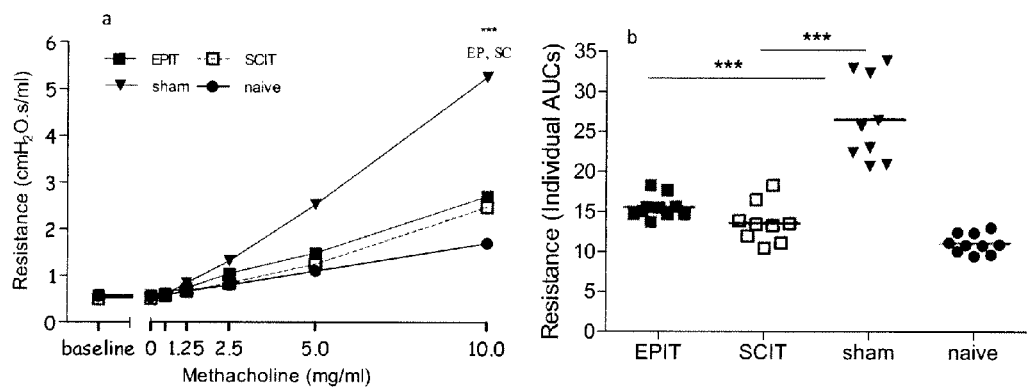
FIG. 16: AHR measured by dynamic resistance 24 h after aerosol challenge to peanut. (a) Dose-response curves obtained for each group and (b) individual area under the curve (AUC) calculated from data of graph (a). EPIT: epicutaneous treated group, SCIT: subcutaneous treated group, sham treated group, naive group. * $p<0.0$ and *** $p<0.001$.

Resistance-compliance (FIG. 16)

At the higher methacholine concentration (i.e. 10 mg/ml), bronchial resistance was dramatically increased in sham group as compared to controls ($p<0.001$), EPIT ($p<0.001$) and SCIT ($p<0.001$). AUC for resistance was significantly lower with EPIT and SCIT than with sham, and did not differ from naïve.

Cytokine Levels and Cell Composition in Blood and BAL Fluid

Figure 17:
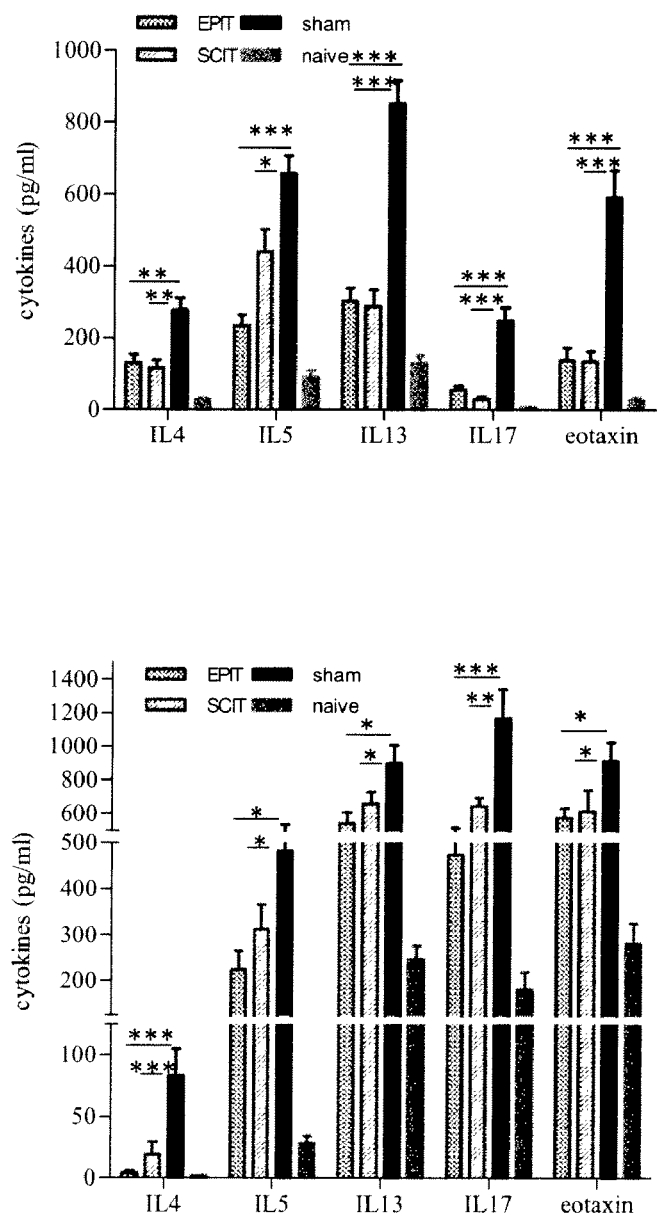
FIG. 17: Inflammatory cytokine levels in BAL fluid (a) and serum (b) of mice challenged to peanut by aerosol. EPIT: epicutaneous treated group, SCIT: subcutaneous treated group, sham: sham group, naive group. Data are means ±SEM for each group of 10 mice, * $p<0.05$,  $p<0.01$ and * $p<0.001$.
Figure 18A:
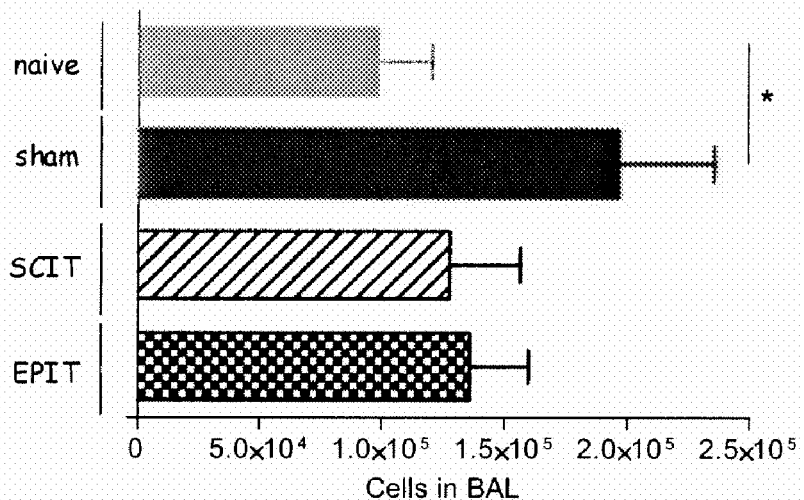
FIG. 18: Number of inflammatory cells in BAL fluid 48 h after the last aerosol challenge to peanut: (a) macrophages, (b) neutrophils, (c) eosinophils and (d) lymphocytes. EPIT: epicutaneous treated group, SCIT: subcutaneous treated group, sham treated group, naive group. Data are means ±SEM for each group of 10 mice, * $p<0.05$,  $p<0.01$ and * $p<0.001$.
Figure 18B:
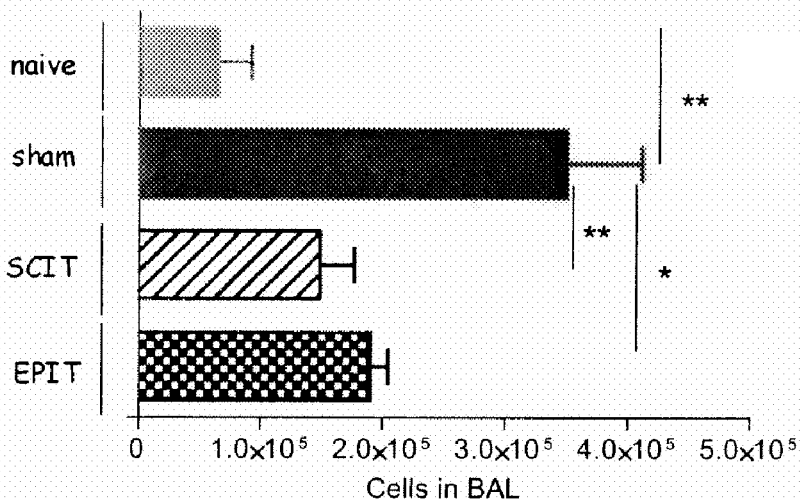
Figure 18C:
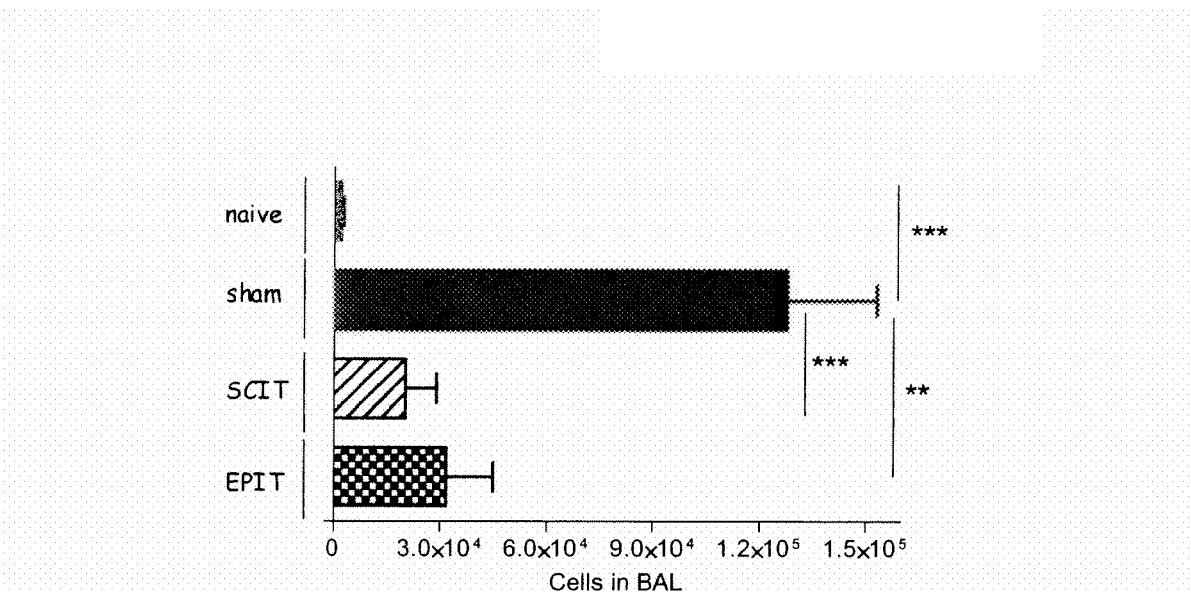
Figure 18D:
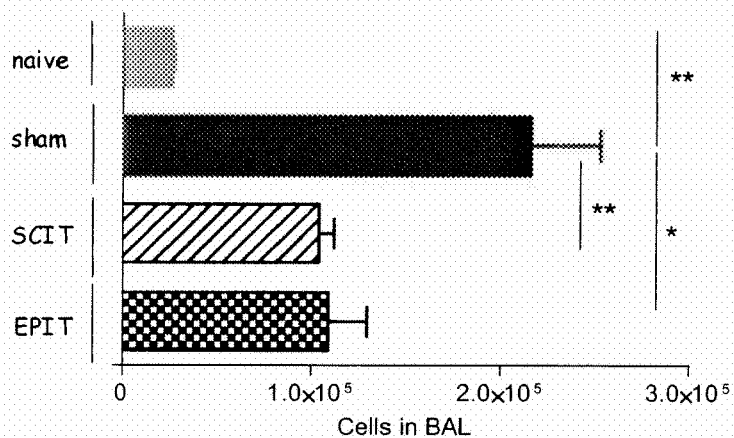

Results for IL-4, IL-5, IL-13, IL-17 and eotaxin are presented in FIGS. 17a (BAL fluid) and 17b (serum).

The BAL fluid and serum of sham mice showed high levels of eotaxin, IL-4, IL-5, IL-13 and IL-17. EPIT and SCIT induced a significant decrease of eotaxin, IL-4, IL-5, IL-13 and IL-17 in both the BAL fluid and serum.

IFN-γ, IL-10 and TNF-α levels were very low in BAL fluid. EPIT and SCIT did not modify the serum levels of IFN-γ and IL-10 (data not shown) but significantly decreased TNF-α levels (respectively 380.2±84.16 pg/ml, $p<0.01$, and 219.9±21.9 pg/ml, $p<0.05$), as compared to sham (881.9±153.6 pg/ml). TGF-β was measurable but without any significant difference between treated (EPIT and SCIT) and sham groups: respectively 270.0∓10.5 pg/ml, 292.7±19.2 pg/ml and 260±17.3 pg/ml in BAL and 147.2±13.1 pg/ml, 198.8±27.2 pg/ml and 133.8±17.5 pg/ml in serum. TGF-β values measured in BAL fluid and serum of treated groups were not different from those of naïve mice (respectively 129.2±10.2 pg/ml and 136.0±13.1 pg/ml).

Forty-eight hours after the last challenge, sensitized mice showed eosinophilia with concomitant increase in neutrophils, lymphocytes and macrophages (FIG. 18). In agreement with their decreased eotaxin levels in BAL fluid, EPIT decreased significantly the number of eosinophils. EPIT also decreased the recruitment of neutrophils and lymphocytes but did not decrease BAL macrophages.

B3. Discussion

The development of EPIT needs reliable safety and efficacy data, especially in food allergy. For obvious ethical reasons, animal models are first needed to evaluate its potential efficacy. Here, we used a model of mice orally sensitized to peanut and explored a new immunotherapy method consisting in the use of an original EDS for repeated and prolonged applications of allergen to the non-stripped skin. We observed a shift in serum antibody isotypes and a reduction in airway hyperresponsiveness and lung eosinophilia.

The protocol of sensitization, already validated by Adel-Patient et al., was based on weekly oral administrations to 3 weeks old BALB/c mice of peanut protein extract (PPE) combined with cholera toxin during 6 weeks. As observed in the current study, this protocol allows optimal sIgE induction. In opposition to previous experiments where skin had been previously stripped (Strid et al), EDS was here applied to intact skin. The preparation of the skin was such as to avoid any alteration of its barrier properties.

EPIT induced a major decrease of sIgE together with an increase of sIgG2a; sIgG1 remained unchanged. SCIT achieved similar results. In a comparable study with OVA-sensitized mice, SCIT administered twice a week for 8 weeks increased serum levels of ovalbumin-specific IgE, IgG1 and IgG2a until the 5$^{th}$ week of treatment. Then, sIgE levels decreased sharply, while sIgG2a continued to increase and sIgG1 continued to increase for 2 additional weeks before starting to decrease. Thus, the antibody pattern of the present study is very close to the immunological changes observed after 8 weeks of SCIT in this OVA experiment, further confirming that the epicutaneous route induces the same level of immunological changes as the subcutaneous one.

Poulsen et al., *Comparison of intestinal anaphylactic reactions in sensitized mice challenged with untreated bovine milk and homogenized bovine milk,* 45(5) ALLERGY 321, 321-26 (1990) demonstrated very early that intestinal anaphylaxis after oral challenge is associated with the release of histamine and other mediators leading to acute systemic symptoms. In previous experiments with various allergens, mice did not exhibit any anaphylactic symptoms clinically measurable. We thus performed a histamine provocation test. The absence of significant increase of histamine in the treated group after oral challenge with PPE illustrates the ability of EPIT to prevent mastocyte degranulation.

To date, the in vivo measurement of respiratory function in mice is based on both non-invasive and invasive approaches. Whole body plethysmography is non invasive and has been used in various mouse models of allergy. It allows recording the pressure fluctuations that occur during the breathing cycle of mice and measures a single parameter called Penh. However, Penh may be strongly influenced by events unrelated to lung mechanics such as hyperoxia, the timing of ventilation and humidification and warming of inspired gas. The compliance-resistance measurement technique is invasive but offers the key advantage of combining orotracheal intubation via direct laryngoscopy and local administration of allergenic extracts directly into the lung. Bronchoconstriction is assessed by the "gold standard" parameters, airway resistance and dynamic compliance, in response to aerosolized methacholine or allergens in anesthetized mice. Hoymann H G., *New developments in lung function measurements in rodents*, 2 EXP. TOXICOL. PATHOL. 5, 5-11 (2006). This method also could be performed using increasing doses of methacholine. It has been validated in several groups of BALB/c mice and is considered as reproducible without causing alteration in the BAL fluid.

Actually, a combination of invasive and non-invasive techniques is most often required to fully understand the physiological significance of respiratory phenotype. This option was retained in the present study. Treatment dramatically improved the respiratory condition of sensitized animals and the results appeared to be highly concordant with all techniques.

In line with these results, EPIT and SCIT decreased the IgG1/IgG2a ratio and decreased serum eotaxin and $T_H2$-related cytokines (IL-4, IL-5 and IL-13). Overall, these changes reflect the switch of the immune response from a $T_H2$ to a balanced $T_H2/T_H1$ profile. The switch to a $T_H1$ profile accompanying an increased tolerance to peanut has also been established in humans. Indeed, comparing the cytokine-producing phenotypes of peanut-specific lymphocytes from children who had outgrown peanut allergy and from children who had always tolerated peanuts, Turcanu showed that peanut antigens induced a $T_H2$-biased response in peanut allergic children while non allergic ones exhibited a $T_H1$ skewed response. Turcanu et al., *Characterization of lymphocyte responses to peanuts in normal children, peanut allergic children and allergic children who acquired tolerance to peanuts*, 111(7) J. CLIN. INVEST. 1065, 1065-72 (2003). Moreover, the resolution of peanut allergy was accompanied by a shift to $T_H1$ cytokine profile.

Another finding is the dramatic decrease of cell recruitment, in particular eosinophils, and the decrease of eotaxin, IL-5 and IL-13 in the lung of treated mice. Eotaxin induces a rapid recruitment of eosinophils in allergen-stimulated tissues. Actually, treatment seems to influence all the steps of the eosinophilic recruitment, from the IL-5-induced release of eosinophils from the bone marrow to the IL-13-favored eosinophil infiltration of the lung, which is responsible for overexpression of eotaxin by lung epithelial cells in allergic mice after challenge.

The intimate mechanisms at the skin level during EPIT need further investigation. In a previous study, we have shown with fluorochrome-conjugated ovalbumin that, after 24 hours of application, the fluorescence detected in the superficial layers of the skin was restricted to allergen presenting cells: more than 80% of the Langherans cells of the epiderm and 50% of the dendritic cells of the derm had captured the allergen (unpublished data). As suggested in studies by Strid et al., this process is the first step of an immune reaction. Strid et al., *Epicutaneous immunization converts subsequent and established antigen-specific T helper type 1 (Th1) to Th2-type responses*, 119(1) IMMUNOLOGY 27, 27-35 (2006). Further studies are needed to determine which exact processes are set up to finally influence the induction of a tolerance immune profile.

In conclusion, these data show that the epicutaneous route is a very potent approach for immunotherapy. These results also show that this new approach for immunotherapy could take additional value in clinical situations where injection or oral consumption might put the patient at risk.

C—Clinical Study in Human Subjects

Study Design:

Phase I, randomized, double-blind, placebo-controlled, safety study. This safety study is conducted using 3 age groups (adults, teenagers and children) randomized sequentially (adults first, teenagers in second and children last) to test 2 different dosing regimens and 4 doses of peanut protein versus placebo during a 2-week treatment period. Eight cohorts of 5 adults with an anaphylaxis grade $\leq 4$ (40 adults)+2 cohorts of Grade 5 anaphalaxis subjects (10 adults)+2 cohorts of 5 teenagers (10 teenagers)+2 cohorts of 5 children (10 children) participate in this study. 2 additional cohorts of teenagers or 2 additional cohorts of children may be added distinctively if necessary.

Product Description:

The active treatment, named Pn-EPIT, utilizes the VIASKIN® drug delivery system (DBV Technologies) containing a dry deposit of a peanut protein formulation without adjuvant. The peanut allergen extract, containing all peanut proteins and supplied from Greer Laboratories (Lenoir, N.C., USA), is deposited on an occlusive polymer by electrospraying the peanut protein reconstituted extract with constitutive excipients. The placebo treatment is of similar formulation but devoid of peanut protein.

Treatment Description:

Pn-EPIT at the designated dose is applied either for 24 hours each on the external side of the upper arm (with sites rotated every 24 hours clockwise) over a 2-week dosing period (continuous regimen with 14 Viaskins per subject), or is applied each on the external side of the upper arm every other day for 48 hours each (with sites rotated every other day clockwise) over a 2-week dosing period (continuous regimen with 7 Viaskins per subject).

Pn-EPIT or placebo is given first to adult dosing cohorts (ages 18-50 years). Each adult cohort is composed of 5 subjects each randomized 4:1 (active:placebo).

Pn-EPIT or placebo is then given to teenagers dosing cohorts (ages 12-17 years). Each teenager cohort is composed of 5 subjects each randomized 4:1 (active:placebo).

Pn-EPIT or placebo is then given to children dosing cohorts (ages 6-11 years). Each children cohort is composed of 5 subjects each randomized 4:1 (active:placebo).

The first adult cohorts shall receive a dose of peanut protein [based on the maximal recommended starting dose (MRSD) calculation of 5 μg derived from preliminary animal toxicity studies]: 1) i.e. 5 μg peanut protein. The next doses studied are 100 μg peanut protein, 250 μg peanut protein and 500 μg peanut protein. Only if safety issues arise at 100 μg of peanut protein, will an intermediate dose of 50 μg be studied. At each dose tested, one cohort will be under the every day regimen and the second cohort under the every other day regimen.

A 2-week dosing period will allow for analysis of safety based on several factors including immediate reactions (Day 1 to Day 3), more than grade III skin reactions according to the international classification (more than 7 vesicles, or skin ulcerative lesions, lesions spreading beyond the area of application of the Viaskin®), adverse Viaskin® site reactions, changes in blood or general medical safety parameters judged significant by the investigators, and adverse reactions associated with co-morbid disease (e.g., atopic dermatitis or asthma). Cohorts will be studied sequentially to ensure safety with monitoring daily for the first 72 hours (8 hours on day 1; 2 hours on days 2 and 3, observation period can be extended if judged necessary by the investigator) then visits weekly to monitor for adverse effects.

A period of data safety monitoring and analysis of up to 1 full week of treatment shall be utilized after all subjects of the adult cohorts have completed dosing at a dose. This DSMB review ensures safety before escalating to the next dose in the adult cohorts. This process is repeated until the maximum dose is reached in the adult population. Then a sequential progression to the teenager cohorts at the maximum tolerated adult dose will occur. Monitoring and analysis of the safety of the teenager cohorts is done by the DSMB before progressing to the children cohorts at the same dose.

Also, 2 adult cohorts composed solely of subjects with a Grade 5 anaphylaxis history to peanut will be dosed after the safety of adult cohorts with a grade $\leq 4$ has been assessed as satisfactory.

Once the first adult cohorts at 5 µg have completed one week of treatment at both regimens (once a day and every other day), safety data are monitored by the DSMB. The same process will be repeated up to 500 µg or if the maximum tolerated dose is reached before.

Then, the teenager cohorts will be treated at 500 µg or the maximum tolerated adult dose with dosing cohorts receiving Pn-EPIT at 24 hr or 48 hr continuous dosing. Safety data will be available for monitoring by the DSMB. If the treatment is deemed safe for the teenagers, the children cohorts will be treated at 500 µg or the maximum tolerated teenager dose. The teenager cohorts will have to complete their 2 weeks of treatment and the safety analyzed before enrolling the children cohorts at the teenager-tolerated dose.

Pn-EPIT will be applied either for 24 hours or 48 hours depending on the regimen. 48 hour-application will be the maximum duration of application of a Viaskin®.

Repeating the administration of the Viaskins every day or every other day, should allow the subjects to become more and more tolerant. Hence, the possibility to apply Viaskins for longer and longer periods shall be tested until the full duration of application. The total number of days required to reach the recommended full duration of application will be noted for each subject in a cohort.

The invention claimed is:

1. An immunotherapeutic method for increasing tolerance in a subject to groundnut, comprising:
   repeatedly administering to the subject one or more proteins derived from groundnut via an epicutaneous route using a skin patch including a backing having a periphery adapted to create a hermetically closed chamber when applied to the subject's skin,
   the backing carrying said one or more proteins in a dose sufficient to induce an immune reaction in the subject following application of the skin patch to the subject's skin,
   said one or more proteins being removed from the backing following application of the patch device to the subject's skin and thereafter being delivered to the subject via the epicutaneous route,
   said administration leading, on repetition, to a progressive increase in tolerance in the subject to groundnut,
   said one or more proteins being formulated without any adjuvant.

2. A method according to claim 1, wherein said one or more proteins are selected from ARAh1, ARAh2 and ARAh3 optionally in combination with other proteins derived from groundnut.

3. A method according to claim 1, wherein said one or more proteins are administered in the form of an at least partially purified extract of groundnut.

4. A method according to claim 1, wherein said one or more proteins are in dry form.

5. A method according to claim 4, wherein said one or more proteins are in particulate form and attached to the backing without adhesive using electrostatic, Van der Waals forces, or both.

6. A method according to claim 4, wherein said one or more proteins are in particulate form and attached to the backing using an adhesive coating on the backing.

7. A method according to claim 1, further comprising loading said one or more proteins onto the backing by dissolving the proteins in a solvent, disposing the dissolved proteins on the backing, and evaporating the solvent to leave the proteins in particle form.

8. A method according to claim 1, wherein said one or more proteins are dissolved or dispersed in a liquid.

9. A method according to claim 8, wherein said one or more proteins in liquid form are held on the backing in a reservoir of adsorbent material.

10. A method of claim 1, wherein condensation forms within the chamber following application of the patch device to the skin, which causes or enhances removal and epicutaneous delivery of the proteins.

11. The method of claim 10, wherein condensation forms as a result of perspiration.

12. The method of claim 1, wherein the device is applied without pre-treating the skin of the subject.

13. A method according to claim 1, wherein the periphery of the backing has adhesive properties.

14. A method according to claim 1, wherein the periphery of the backing has adhesive properties on moistured skin.

15. A method according to claim 1, wherein said repeatedly administering comprises applying at least one patch, and then applying another at least one patch after a time period of at least 24 hours.

16. A method according to claim 1, which method causes an increase in specific IgG levels.

17. A method according to claim 16, which method causes an increase in specific IgG4 levels.

18. A method according to claim 1, which method causes the raising of a Th1 response to the proteins administered.

19. A method according to claim 1, which method causes an immune deviation from a dominant Th2 profile to a more balanced Th1/Th2 profile.

20. A skin patch comprising:
   a backing having a periphery adapted to create a hermetically closed chamber when applied to skin,
   the backing carrying one or more proteins derived from groundnut in a dose sufficient to induce an immune reaction in a subject following application of the skin patch to the subject's skin,
   said one or more proteins derived from groundnut being removed from the backing following application of the skin patch to the subject's skin and thereafter being delivered to the subject via an epicutaneous route,
   said one or more proteins being formulated without any adjuvant.

21. A kit comprising a plurality of skin patches according to claim 20, each skin patch containing the same amount of groundnut allergen.

* * * * *